(12) United States Patent
Ray et al.

(10) Patent No.: US 10,537,535 B2
(45) Date of Patent: Jan. 21, 2020

(54) HISTONE DEACETYLASE INHIBITORS

(71) Applicant: The Regents of the University of California, Oakland, CA (US)

(72) Inventors: Anandasankar Ray, Riverside, CA (US); Sachiko Yamanaka, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/780,618

(22) PCT Filed: Dec. 2, 2016

(86) PCT No.: PCT/US2016/064815
§ 371 (c)(1),
(2) Date: May 31, 2018

(87) PCT Pub. No.: WO2017/096298
PCT Pub. Date: Jun. 8, 2017

(65) Prior Publication Data
US 2018/0360775 A1    Dec. 20, 2018

Related U.S. Application Data

(60) Provisional application No. 62/263,522, filed on Dec. 4, 2015.

(51) Int. Cl.
*A61K 31/121* (2006.01)
*A61K 48/00* (2006.01)
*A61P 25/28* (2006.01)
*A61K 9/00* (2006.01)

(52) U.S. Cl.
CPC ........... *A61K 31/121* (2013.01); *A61K 9/007* (2013.01); *A61K 9/0043* (2013.01); *A61P 25/28* (2018.01); *A61K 48/00* (2013.01)

(58) Field of Classification Search
CPC .... A61K 31/121; A61K 48/00; A61K 9/0043; A61K 9/007; A61P 25/28; Y02A 50/411
See application file for complete search history.

(56) References Cited

U.S. PATENT DOCUMENTS

| 6,376,508 | B1 | 4/2002 | Li et al. | |
|---|---|---|---|---|
| 2005/0037992 | A1 | 2/2005 | Lyons et al. | |
| 2006/0270730 | A1 | 11/2006 | Katopodis | |
| 2010/0099706 | A1* | 4/2010 | Owoo | A61K 9/0019 514/314 |
| 2012/0004498 | A1 | 1/2012 | Malaspina et al. | |

FOREIGN PATENT DOCUMENTS

| WO | 2002/090534 A1 | 11/2002 |
|---|---|---|
| WO | 2007/049262 A1 | 5/2007 |
| WO | 2017/200194 A2 | 11/2017 |

OTHER PUBLICATIONS

Steffan et al., "Histone deacetylase inhibitors arrest polyglutamine-dependent neurodegeneration in Drosophila," Nature, Oct. 18, 2001; vol. 413: pp. 739-743. (Year: 2001).*
Bolden et al., "Anticancer Activities of Histone Deacetylase Inhibitors", Nature Reviews, Drug Discovery, vol. 5, Sep. 2006, pp. 769-784.
Bruyne et al., "Odor Coding in the Drosophila Antenna", Neuron, vol. 30, May 2001, pp. 537-552.
Chuang et al., "Multiple Roles of HDAC Inhibition in Neurodegenerative Conditions", Trends in Neurosciences, vol. 32 No. 11, 2009, pp. 591-601.
Clark et al., "Diacetyl in Foods: A Review of Safety and Sensory Characteristics", Comprehensive Reviews in Food Science and Food Safety, vol. 14, 2015, pp. 634-643.
Gräff et al., "Histone Acetylation: Molecular Mnemonics on the Chromatin", Nature Reviews, Neuroscience, vol. 14, Feb. 2013, pp. 97-111.
Hallem et al,, "The Molecular Basis of Odor Coding in the Drosophila Antenna", Cell, vol. 117, Jun. 25, 2004, pp. 965-979.
International Preliminary Report on Patentability received for PCT Patent Application No. PCT/US2016/064815, dated Jun. 14, 2018, 12 pages.
International Search Report and Written Opinion received for PCT Patent Application No. PCT/US2016/064815, dated Feb. 8, 2017, 14 pages.
Kazantsev et al., "Therapeutic Application of Histone Deacetylase Inhibitors for Central Nervous System Disorders", Nature Reviews, Drug Discovery, vol. 7, Oct. 2008, pp. 854-868.
Minucci et al., "Histone Deacetylase Inhibitors and the Promise of Epigenetic (and more) Treatments for Cancer", Nature Reviews, Cancer, vol. 6, Jan. 2006, pp. 38-51.
Shahbazian et al., "Functions of Site-Specific Histone Acetylation and Deacetylation", Annual Review of Biochemistry, vol. 76, 2007, pp. 75-100.
Turner et al., "Modification of CO2 Avoidance Behaviour in Drosophila by Inhibitory Odorants", Nature, vol. 461, 2009, pp. 277-281.
Extended European Search Report received for European Patent Application No. 16871665.2, dated Jul. 9, 2019, 10 pages.
Kovacic et al., "Role of Diacetyl Metabolite in Alcohol Toxicity and Addiction Via Electron Transfer and Oxidative Stress", Archives of Toxicology, vol. 79, 2005, pp. 123-128.
Waldecker et al., "Inhibition of Histone-Deacetylase Activity by Short-Chain Fatty Acids and Some Polyphenol Metabolites Formed in the Colon", Journal of Nutritional Biochemistry, vol. 19, 2008, pp. 587-593.

* cited by examiner

Primary Examiner — Sahar Javanmard
(74) Attorney, Agent, or Firm — Morrison and Foerster LLP

(57) ABSTRACT

Provided herein are compounds that act as histone deacetylase (HDAC) inhibitors, and can affect expression of genes in vivo and in vitro. These HDAC inhibitors are generally volatile compounds that can be administered as a gas or vapor. Such inhibitors can be used as therapeutics for numerous disease conditions, such as a variety of cancers, neural degenerative diseases, neurological diseases, senescence, and infectious diseases.

5 Claims, 21 Drawing Sheets

Upregulated in antenna RNAseq

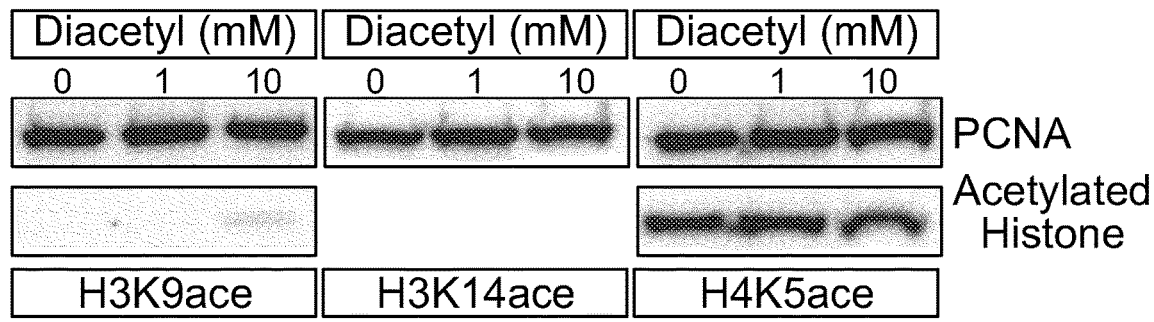
FIG. 5A
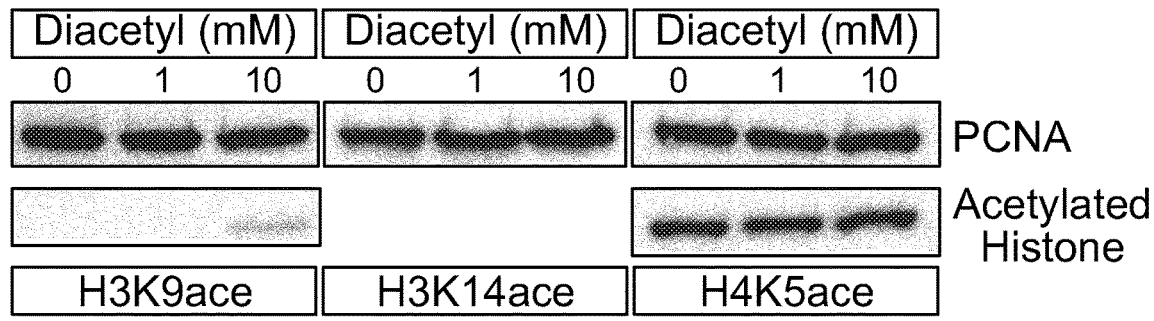
FIG. 5B
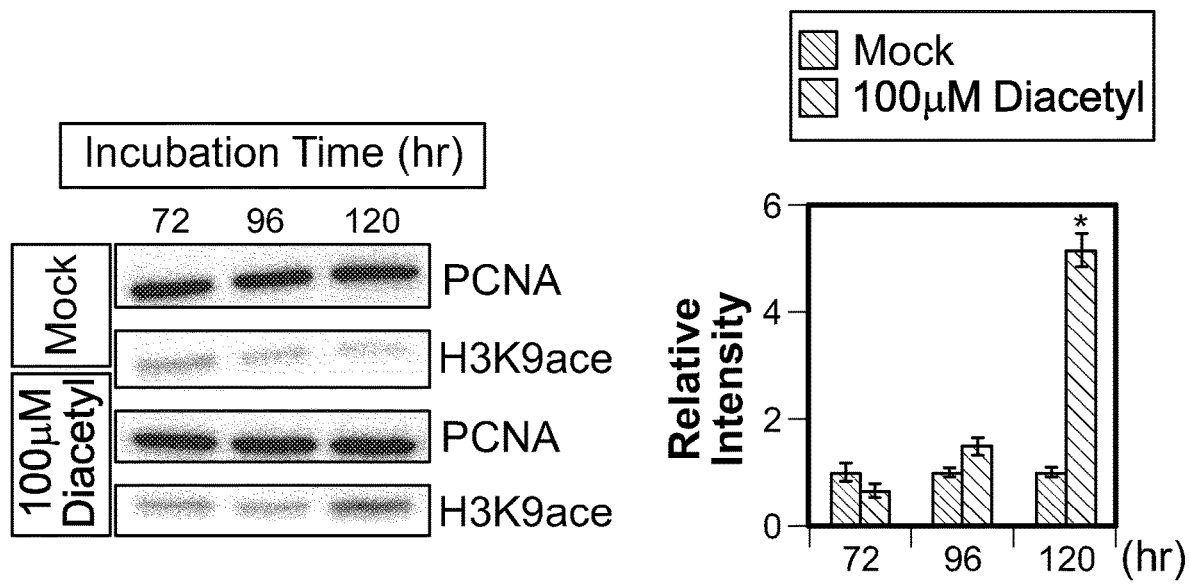
FIG. 5C  FIG. 5D

Solvent vs Diacetyl DEG (up): 125 Genes

< Categoly I >
D > RD

< Categoly II >
D ~ RD ~ RP

< Categoly IV >
D ~ RD < RP

< Categoly III >
D < RD

HISTONE DEACETYLASE INHIBITORS

CROSS-REFERENCE TO RELATED APPLICATIONS

This application is a National Phase application under 35 U.S.C. 371 of International Application No. PCT/US2016/064815, filed Dec. 2, 2016, which claims priority to U.S. Provisional Patent Application No. 62/263,522, filed Dec. 4, 2015, the disclosures of each of which are incorporated herein by reference in their entireties.

FIELD

The present disclosure relates generally to compounds that inhibit histone deacetylase (HDAC), and methods of identifying and using such compounds, and more specifically to volatile compounds that inhibit HDAC.

BACKGROUND

Histone deacetylases (HDACs) are involved in the regulation of DNA expression. They are implicated in many diseases, such as neurological disorders (e.g., Huntington's disease, Alzheimer's disease, Parkinson's disease, multiple sclerosis, and dementia), cancer, and chronic obstructive pulmonary disorder (COPD). HDACs are also involved in immune responses to infectious disease.

HDAC, inhibitors are histone-modifying enzymes involved in the removal of acetyl groups from lysine residues and the remodeling of chromatin structure, which has a key role in the epigenetic regulation of gene expression (Graff, J., and Tsai, L. H. (2013). Histone acetylation: molecular mnemonics on the chromatin. Nat Rev Neurosci 14, 97-111; Shahbazian, M. D., and Grunstein, M. (2007). Functions of site-specific histone acetylation and deacetylation. Annu Rev Biochem 76, 75-100). Because of their dramatic impact on gene regulation, HDAC inhibitors are promising targets in drug development for many diseases such as cancers and neurodegenerative disorders (Bolden, J. E., Peart, M. J., and Johnstone, R. W. (2006). *Anticancer activities of histone deacetylase inhibitors*. Nat Rev Drug Discov 5, 769-784; Chuang, D. M., Leng, Y., Marinova, Z., Kim, H. J., and Chiu, C. T. (2009). *Multiple roles of HDAC inhibition in neurodegenerative conditions*. Trends Neurosci 32, 591-601; Kazantsev, A. G., and Thompson, L. M. (2008). *Therapeutic application of histone deacetylase inhibitors for central nervous system disorders*. Nat Rev Drug Discov 7, 854-868; Minucci, S., and Pelicci, P. G. (2006). *Histone deacetylase inhibitors and the promise of epigenetic (and more) treatments for cancer*. Nat Rev Cancer 6, 38-51). Indeed, several classes of HDAC inhibitors administered orally have been found to attenuate the progression of a repertoire of cancers and neurodegenerative diseases including Alzheimer's disease and Huntington's disease (Chuang, D. M., Leng, Y., Marinova., Z., Kim, H. J., and Chiu, C. T. (2009). *Multiple roles of HDAC inhibition in neurodegenerative conditions*. Trends Neurosci 32, 591-601).

In particular, neurodegeneration and neuronal senescence in mammals is often associated with the accumulation of heterochromatin, which may lead to down-regulation of neuronal gene expression involved in learning and memory. There are challenges to identify effective therapeutics for neurological conditions, for example due to a lack of protein targets or the difficulty identifying drugs that can cross the blood-brain barrier. The epigenetic machinery, such as HDAC, involved in disease processes is one avenue that may have great effects in developing treatments. One method of modulating HDAC is through the use of HDAC inhibitors.

Thus, methods of identifying new classes of volatile histone deacetylase inhibitors, and methods of using such histone deacetylase inhibitors for the prophylaxis and treatment of diseases and disorders, are needed in the art.

BRIEF SUMMARY

In some aspects, provided is a method of treating, or delaying the development of, a disease or disorder in a subject in need thereof, by administering to the subject an effective amount of a histone deacetylase (HDAC) inhibitor compound. Such disease or disorder may include, for example, a neurological disorder, cancer, chronic obstructive pulmonary disorder (COPD), or an infectious disease. In one variation, the neurological disorder is Huntington's disease, Alzheimer's disease, Parkinson's disease, multiple sclerosis, or dementia. In some variations, the HDAC inhibitor compound is administered as a gas or vapor.

In other aspects, provided is a method of treating, or delaying the development of, neurodegeneration in a subject in need thereof, by administering to the subject an effective amount of a histone deacetylase (HDAC) inhibitor compound to treat neurodegeneration in the subject.

In yet other aspects, provided is a method of modulating gene expression in neurons in a subject in need thereof, comprising administering to the subject an effective amount of a histone deacetylase (HDAC) inhibitor compound to modulate gene expression in the neurons of the subject.

In certain aspects, provided is a method of improving immune response in a subject in need thereof, comprising administering to the subject an effective amount of a histone deacetylase (HDAC) inhibitor compound to improve the immune response of the subject.

In yet other aspects, provided is a method of inhibiting histone deacetylase (HDAC) in a subject in need thereof, comprising administering the subject an effective amount of a HDAC inhibitor compound to inhibit HDAC in the subject.

In some embodiments of the foregoing aspects, the subject is a human.

In other variations, the HDAC inhibitor compound is formulated as a pharmaceutical composition, which further includes at least one pharmaceutically acceptable excipient.

In other aspects, provided herein are also kits that include at least one of the HDAC inhibitor compounds described herein, or a pharmaceutically acceptable salt, prodrug, or solvate thereof, and suitable packaging. In one embodiment, a kit further includes instructions for use. In one embodiment, a kit includes at least one of HDAC inhibitor compounds described herein, or a pharmaceutically acceptable salt, prodrug, or solvate thereof, and a label and/or instructions for use of the compounds in treatment of the indications, including the diseases or disorders described herein.

In yet other aspects, provided herein are also articles of manufacture that include at least one of the HDAC inhibitor compounds described herein, or a pharmaceutically acceptable salt, prodrug, or solvate thereof, in a suitable container. The container may be a vial, jar, ampoule, preloaded syringe, and intravenous bag.

DESCRIPTION OF THE FIGURES

The present application can be best understood by reference to the following description taken in conjunction with the accompanying figures, in which like parts may be referred to by like numerals.

FIG. 3A depicts a schematic of odor exposure protocol for transcriptome analysis from the antennae. FIG. 3B depicts a scatter plot comparing log 2 mean read counts from diacetyl-exposed versus paraffin oil (PO)-exposed samples. X-axis, log 2 mean read counts of genes in PO samples. Y-axis, mean read counts of genes in diacetyl samples. Red dots showing differentially expressed genes with padj<0.01. FIG. 3C depicts a volcano plot showing enrichment of up- and down-regulated genes in diacetyl-exposed group. X-axis, log 2 fold change (LFC). Y-axis, −log 10 adjusted p value (padj). Red and blue dots represent up-regulated genes (padj<0.01, LFC>1) and down-regulated genes (padj<0.01, LFC<1), respectively. FIG. 3D depicts two pie charts showing Gene Ontology (GO)-slim terms of molecular function in up- (left) and down-regulated (right) genes. FIGS. 3E and 3F depict bar graphs showing overrepresented GO terms in up- (E) and down-regulated (F) gene lists compared to all *D. melanogaster* genes listed in FlyBase (p<0.05). X-axis, GO terms overrepresented in diacetyl-stimulated group. Y-axis, log 10 fold enrichment compared to all FlyBase genes.

FIG. 4A depicts chemical structures of diacetyl (left) and β-hydroxybutyrate (right). FIGS. 4B-4E depict dose-activity curves of HDAC1, HDAC2, HDAC3 and HDC8 treated with various concentrations of diacetyl. IC50s are indicated in the chart areas. Error bars, S.E.M., n=4-5.

FIGS. 5A-5D demonstrate that HDAC inhibitory diacetyl causes increased H3K9 acetylation in vivo. FIGS. 5A and 5B depict Western blots showing acetylation levels of H3K9 (left), H3K14 (middle) and H4K5 (right) in HEK293 cells after 2 (A) and 6 (B) hours of diacetyl treatment. PCNA (Proliferating cell nuclear antigen) is a 29 kDa nuclear protein used as a loading control for nuclear protein extracts. FIG. 5C depicts Western blots showing acetylation levels of H3K9 in HEK293 cells treated with 100 µM diacetyl for 3-5 days. PCNA is used for a loading control. FIG. 5D depicts a bar graph showing the relative intensities of acetylated H3K9. Error bars, S.E.M., n=4 samples. *, p<0.01 by t test against mock at each time point.

FIG. 6A depicts a schematic illustration of the HDAC inhibitor treatment in food for transcriptome analysis from the antennae. FIGS. 6B and 6C depicts volcano plots showing enrichment of up- and down-regulated genes in sodium butyrate-(B) and valproic acid-treated (C) groups. X-axis, log 2 fold change (LFC). Y-axis, −log 10 adjusted p value (padj). Red and blue dots represent up-regulated genes (padj<0.01, LFC>1) and down-regulated genes (padj<0.01, LFC<1), respectively. FIGS. 6D and 6E depict Venn diagrams showing the overlaps of up- (p) and down-regulated (E) genes among diacetyl-, sodium butyrate- and valproic acid-treated groups. FIGS. 6F and 6G depict heat maps showing log 2 RPKM of the genes commonly up- (F) and down-regulated (G) in diaceyl-, sodium butyrate- and valproic acid-treated groups. FIGS. 6H and 6I depict bar graphs showing overrepresented GO terms in commonly up- (H) and down-regulated (I) gene lists compared to all *D. melanogaster* genes listed in FlyBase (p<0.05). X-axis, overrepresented GO terms. Y-axis, log 10 fold enrichment compared to all FlyBase genes.

FIG. 7A depicts a schematic illustration of odor exposure and recovery experiment for transcriptome analysis from the antennae. FIG. 7B depicts volcano plots showing enrichment of up- and down-regulated genes in diacetyl-recovery group (RD) compared to paraffin oil-exposed group (RP). X-axis, log 2 fold change (LFC). Y-axis, −log 10 adjusted p value (padj). Red and blue dots represent up-regulated genes (padj<0.01, LFC>1) and down-regulated genes (padj<0.01, LFC<1), respectively. FIG. 7C depicts heat maps showing log 2 RPKM of the genes up regulated in diacetyl-exposed group at day 5.

FIG. 8A depicts a schematic diagram showing temperature of experimental condition and timing of the eye examination in pGMR-HTTQ120 flies. FIG. 8B depicts a bar graph showing mean number of rhabdomeres in an ommatidium in vehicle-(blue) and diacetyl-exposed (red) pGMR-HTTQ120 flies at 1, 5 and 10 days after eclosion (AE). Error bars, S.E.M., n=600 ommatidia from 15 flies. *, p<0.01 by I test against PO-treated flies at each time point. FIG. 8C depicts a representative image of ommatidia of pGMR-HTTQ120 flies at 1 day AE. FIGS. 8D and 8E depicts representative images of ommatidia of pGMR-HTTQ120 flies exposed to PO (left) or diaceyl (right) at 5 days AE (D) and 10 days AE (E). FIGS. 8F and 8G depict bar graphs showing the percent of the ommatidium with a given number of rhabdomeres in x-axis.

FIG. 10A depicts volcano plots showing enrichment of up- and down-regulated genes in paraffin oil-recovery group (RP) compared to 5 day paraffin oil-exposed group (PO). X-axis, log 2 fold change (LFC). Y-axis, −log 10 adjusted p value (padj). Red and blue dots represent up-regulated genes (padj<0.01, LFC>1) and down-regulated genes (padj<0.01, LFC<1), respectively. FIG. 10B depicts volcano plots showing enrichment of up- and down-regulated genes in diacetyl-recovery group (RP) compared to 5 day diacetyl-exposed group. FIG. 10C depicts Venn diagrams showing the overlaps of up- (top) and down-regulated (bottom) genes between diacetyl-recovery (RD) and diacetyl-exposed groups.

DETAILED DESCRIPTION

Figure 1A:
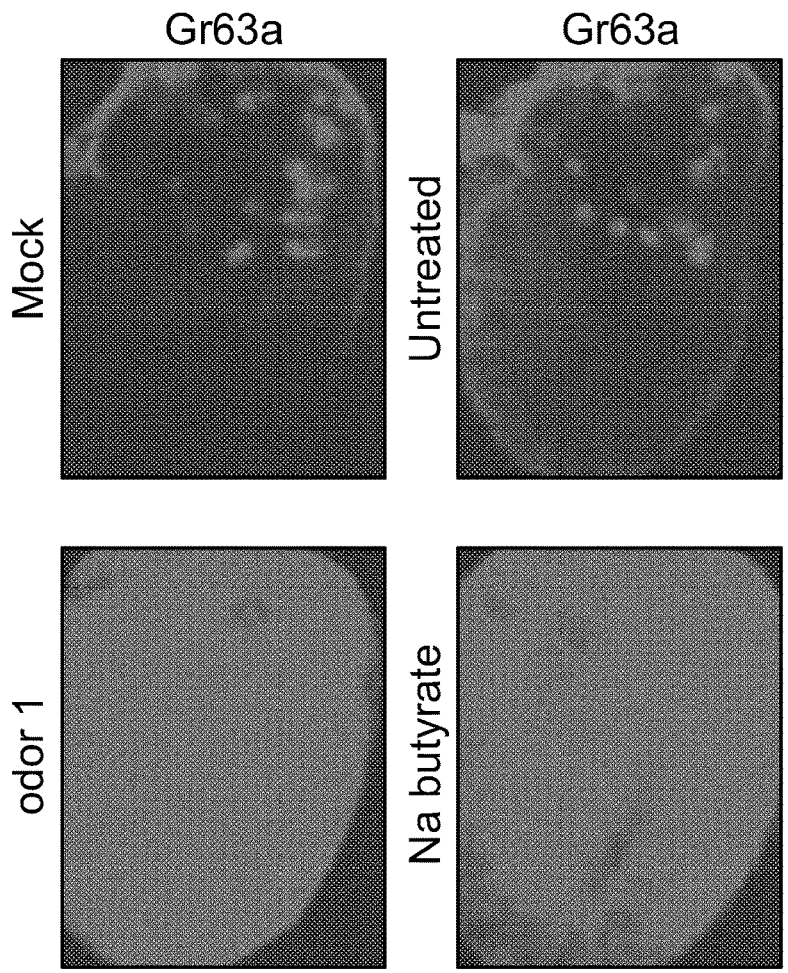
FIG. 1A depicts whole mount RNA in situ images of adult *Drosophila* antenna Gr63a showing overexpression after mock exposure (top left), untreated (top right), 5 days of exposure to odor 1 (diacetyl; bottom left), and after feeding sodium butyrate (bottom right).

The following description sets forth exemplary methods, parameters and the like. It should be recognized, however, that such description is not intended as a limitation on the scope of the present disclosure but is instead provided as a description of exemplary embodiments.

The present application is directed to histone deacetylase (HDAC) inhibitors and their use in therapeutic treatment. Provided herein are odorant and tastant compounds that acts as HDAC inhibitors, and can affect expression of genes in vivo and in vitro. These odorant and tastant HDAC inhibitors can be used as therapeutics for numerous disease conditions, such as a variety of cancers, neural degenerative diseases, neurological diseases, senescence, and infectious diseases.

In one aspect, provided herein are methods of identifying compounds that are histone deacetylase (HDAC) inhibitors. In another aspect, provided herein are methods treating a disease or disorder in a subject in need thereof, by administering at least one histone deacetylase (HDAC) inhibitor compound to a subject in need thereof to treat the disease or disorder in the subject. In yet another aspect, provided herein are methods of preventing or delaying a disease or disorder by administering at least one histone deacetylase (HDAC) inhibitor compound to a subject in need thereof to prevent or delay the disease or disorder in the subject. In some variations of the foregoing aspects, the subject is a mammal. In one variation of the foregoing aspects, the subject is a human.

HDAC Inhibitor Compounds

It is the present application that recognized expression of hundreds of genes in the antenna of *Drosophila melanogaster* model can be modulated by prolonged exposure to volatile diacetyl, a naturally-occurring odor in a variety of human food sources including butter, wine, yogurt and beer, and that further demonstrated this food-derived odor is able to inhibit histone deacetylases (HDACs) directly. According to one embodiment of the present application, an HDAC inhibitor compound is diacetyl. In some embodiments, HDAC inhibitor compounds are selected from Compounds 1 to 27 listed in Table 1 herein.

In some variations, the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, acetic acid, propionic acid, 2,3-pentanedione, 2-butanon, diacetyl, or any combinations thereof.

In certain variations, the HDAC inhibitor is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, acetic acid, propionic acid, 2,3-pentanedione, 2-butanone, diacetyl. In one variation, the HDAC inhibitor is diacetyl.

Any combinations of the HDAC inhibitors described herein may be used in the methods described herein. In some embodiments, one HDAC inhibitor is used. In other embodiments, two HDAC inhibitors are used. In yet other embodiments, three HDAC inhibitors are used. In some variations, at least two, at least three, or at least four HDAC inhibitors are used in the methods described herein.

In some variations, the HDAC inhibitor is an odorant or a tastant. According to some embodiments of the present application, a volatile compound can be a compound that has a vapor pressure of greater than 0.0001 mg Hg (or greater than 0.0005 mg Hg, 0.001 mg Hg, or 0.01 mg Hg) at 25° C. In certain variations, the HDAC inhibitor is a volatile compound. In one variation, the HDAC inhibitor is a volatile compound inhaled as a gas or vapor. The administration of the HDAC inhibitors described herein as volatile compounds (e.g., administered nasally) may change gene expression in the subject.

Methods of Using HDAC Inhibitor Compounds

Provided are methods of using compounds that have the effect of inhibiting HDAC. In some variations, a pharmaceutically acceptable salt, prodrug, or solvate of such compounds may be used. Thus, in one aspect, provided is a method of inhibiting histone deacetylase (HDAC) in a subject in need thereof, by administering the subject an effective amount of a HDAC inhibitor compound, or a pharmaceutically acceptable salt, prodrug, or solvate thereof. The compounds described herein, or a pharmaceutically acceptable salt, prodrug, or solvate thereof, that have the effect of inhibiting HDAC may be used for the treatment of a disease or disorder in a subject in need thereof. Thus, in another aspect, provided is a method of treating a disease or disorder in a human in need thereof, comprising administering to the human an effective amount of a histone deacetylase (HDAC) inhibitor compound, or a pharmaceutically acceptable salt, prodrug, or solvate thereof, wherein the disease is treated.

In some variations, "inhibition" indicates a decrease in the baseline activity of a biological activity or process. In certain variations, "inhibiting HDAC" refers to a decrease in activity of HDAC as a direct or indirect response to the presence of the compounds described herein, or a pharmaceutically acceptable salt, prodrug, or solvate thereof relative to the activity of HDAC in the absence of such compounds, or a pharmaceutically acceptable salt, prodrug, or solvate thereof.

In some variations, "treatment" or "treating" is an approach for obtaining beneficial or desired results including clinical results. Beneficial or desired clinical results may include one or more of the following:

(i) inhibiting the disease or condition (e.g., decreasing one or more symptoms resulting from the disease or condition, and/or diminishing the extent of the disease or condition);

(ii) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or (iii) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

In some variations, "effective amount" intends such amount of a compound, or a pharmaceutically acceptable salt, prodrug, or solvate thereof, which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

Provided are also methods of using the HDAC inhibitors described herein for the prevention of a disease or disorder in a subject in need thereof. Provided are methods of using the HDAC inhibitors described herein for delaying the development of a disease or disorder in a subject in need thereof. In certain aspects, provided is a method of delaying the development of neurodegeneration in a subject in need thereof, by administering to the subject an effective amount of a histone deacetylase (HDAC) inhibitor compound, or a pharmaceutically acceptable salt, prodrug, or solvate thereof, to treat neurodegeneration in the subject.

In some variations, "delaying" the development of a disease or condition means to defer, hinder, slow, retard, stabilize, and/or postpone development of the disease or condition. This delay can be of varying lengths of time, depending on the history of the disease or condition, and/or subject being treated. For example, a method that "delays" development of a disease or condition is a method that reduces probability of disease or condition development in a given time frame and/or reduces the extent of the disease or condition in a given time frame, when compared to not using the method. Such comparisons are typically based on clinical studies, using a statistically significant number of subjects. Disease or condition development can be detectable using standard methods, such as routine physical exams, mammography, imaging, or biopsy. Development may also refer to disease or condition progression that may be initially undetectable and includes occurrence, recurrence, and onset.

Histone deacetylase (HDAC) includes a family of enzymes that remove acetyl groups from a protein, for example, the ε-amino groups of lysine residues at the N-terminus of a histone. In some variations, the HDAC can be a human HDAC, including, HDAC1, HDAC2, HDAC4, HDAC5, HDAC6, HDAC7, HDAC8, HDAC9, HDAC10, and HDAC11. In other variations, the HDAC also can be derived from a protozoal or fungal source. HDAC inhibitors typically contain three structural elements which are analogous to the structure of acetyllysine. These three structural elements are a zinc binding group (M), which is responsible for chelation of zinc in the active site, a linker region (L), which binds to the hydrophobic channel that connects the active site to the outer enzyme surface, and a capping group (Cap), which interacts with residues at the outer enzyme surface.

Provided herein are compounds that inhibit a histone deacetylase (HDAC), or a pharmaceutically acceptable salt, prodrug, or solvate thereof. In some embodiments, the HDAC inhibitor compounds described herein, or a pharmaceutically acceptable salt, prodrug, or solvate thereof, are used to inhibit HDAC in a subject in need thereof. In some embodiments, the HDAC inhibitor compounds described herein, or a pharmaceutically acceptable salt, prodrug, or solvate thereof, are used in treating or delaying the development of a disease of disorder in a subject in need thereof. In some embodiments, the HDAC inhibitor compounds described herein, or a pharmaceutically acceptable salt, prodrug, or solvate thereof, are used in treating a disease or disorder which is responsive to inhibition of histone deacetylase (HDAC).

In some variations, a disease or disorder that is responsive to inhibition of histone deacetylase (HDAC) includes a condition in which HDAC and/or the action of HDAC is important or necessary, e.g., for the onset, progress, expression of that disease or disorder, or a disease or a disorder which is known to be treated by an HDAC inhibitor (such as, e.g., TSA, pivalolyloxymethylbutane (AN-9; Pivanex), FK-228 (Depsipeptide), PXD-101, NVP-LAQ824, SAHA, MS-275, and or MGCD0103). Examples of such conditions include, but are not limited to, cancer, psoriasis, fibroproliferative disorders (e.g., liver fibrosis), smooth muscle proliferative disorders (e.g., atherosclerosis, restenosis), neurodegenerative diseases (e.g., Alzheimer's, Parkinson's, Huntington's chorea, amyotropic lateral sclerosis, spinocerebellar degeneration, Rett syndrome), peripheral neuropathies (Charcot-Marie-Tooth disease, Giant Axonal Neuropathy (GAN)), inflammatory diseases (e.g., osteoarthritis, rheumatoid arthritis, colitis), diseases involving angiogenesis (e.g., cancer, rheumatoid arthritis, psoriasis, diabetic retinopathy), hetnatopoietic disorders (e.g., anemia, sickle cell anemia, thalasseimia), fungal infections, parasitic infections (e.g., malaria, trypanosomiasis, helminthiasis, protozoal infections), bacterial infections, viral infections, and conditions treatable by immune modulation (e.g., multiple sclerosis, autoimmune diabetes, lupus, atopic dermatitis, allergies, asthma, allergic rhinitis, inflammatory bowel disease; and for improving grafting of transplants).

According to some embodiments of the present application, the disease or disorder is a neurological disorder, cancer, chronic obstructive pulmonary disorder (COPD), or an infectious disease. In certain variations, the disease or disorder is a neurological disorder. In some variations, the neurological disorder is Huntington's disease, Alzheimer's disease, Parkinson's disease, multiple sclerosis, or dementia.

Neurodegeneration and neuronal senescence in mammals may be associated with the accumulation of heterochromatin, which may lead to down-regulation of neuronal gene expression involved in learning and memory. The administration of the HDAC inhibitors described herein may modulate gene expression through inhibition of histone deacetylation. Such modulation may be advantageously achieved by HDAC inhibitors described herein. Thus, in certain aspects, provided is a method of modulating gene expression in neurons in a subject in need thereof, by administering to the subject an effective amount of a histone deacetylase (HDAC) inhibitor compound to modulate gene expression in the neurons of the subject.

The HDAC inhibitor compounds described herein, or a pharmaceutically acceptable salt, prodrug, or solvate thereof, may also modulate gene expression in neurons and/or improving immune response in subjects administered such compounds. Thus, in certain aspects, provided is a method of modulating gene expression in neurons in a subject in need thereof, by administering to the subject an effective amount of a histone deacetylase (HDAC) inhibitor compound, or a pharmaceutically acceptable salt, prodrug, or solvate thereof, to modulate gene expression in the neurons of the subject. In other aspects, provided is a method of improving immune response in a subject in need thereof, by administering to the subject an effective amount of a histone deacetylase (HDAC) inhibitor compound, or a pharmaceutically acceptable salt, prodrug, or solvate thereof, to improve the immune response of the subject.

In other embodiments, provided are methods of increasing levels of H3K9 acetylation in nuclei of cells in a subject, by administering to the subject an effective amount of a histone deacetylase (HDAC) inhibitor compound, or a pharmaceutically acceptable salt, prodrug, or solvate thereof, to the subject.

In some embodiments of the foregoing, the subject is a mammal. In one embodiment of the foregoing, the subject is a human.

The HDAC inhibitor compounds, or a pharmaceutically acceptable salt, prodrug, or solvate thereof, may be administered to the subject as a pharmaceutical composition. In some variations, the pharmaceutical composition includes any of the HDAC inhibitor compounds described herein, or any combinations thereof, or a pharmaceutically acceptable salt, prodrug, or solvate thereof; and at least one pharmaceutically acceptable excipient. In some variations, the HDAC inhibitor compound is present in the pharmaceutical composition in an amount between 1% and 5%; between 6% and 10%; between 11% and 30%; between 31% and 50%; or between 50% and 100% (volume/volume). In some variations, the HDAC inhibitor compound is present in the pharmaceutical composition in an amount between 1% and 5%; between 6% and 10%; between 11% and 30%; between 31% and 50%; or between 50% and 100% (weight/volume).

In one variation, "pharmaceutically acceptable" means a material that is not biologically or otherwise undesirable, e.g., the material may be incorporated into a pharmaceutical composition administered to an individual without causing significant undesirable biological effects or interacting in a deleterious manner with any of the other components of the composition in which it is contained.

Further, "excipient" may include an inert or inactive substance used in the production of a drug or pharmaceutical, such as a tablet containing a compound detailed herein, or a pharmaceutically acceptable salt thereof, as an active ingredient.

In some variations, the pharmaceutical composition may take the form suitable for nasal or oral administration. In one variation, the pharmaceutical composition is formulated as a gas or vapor for administration to the subject. In other variations, the pharmaceutical composition may take the form suitable for topical administration.

In one variation, the HDAC compounds, or a pharmaceutically acceptable salt, prodrug, or solvate thereof, are odorant compounds, administered nasally. Odorant HDAC inhibitor compounds of the present invention may modulate HDAC activity, prevent a disease or disorder, or treat a disease or disorder by transport through the olfactory epithelium-lined trans-epithelial nasal pathway. In certain variations, administration of an odorant HDAC inhibitor compound may bypass the blood-brain barrier by transport through the nasal pathway. The odorant HDAC inhibitor compounds may be formulated for any suitable delivery route, and may take the form of, for example, aerosols (e.g., nasal spray or inhalers). In one variation, the HDAC inhibitor compound is formulated for delivery as a gas or vapor.

In another variation, the HDAC compounds, or a pharmaceutically acceptable salt, prodrug, or solvate thereof, are tastant compounds, administered orally. Tastant HDAC inhibitor compounds of the present invention may modulate HDAC activity, prevent a disease or disorder, or treat a disease or disorder by transport by administration through the mouth. The tastant HDAC inhibitor compounds may be formulated for any suitable delivery route, and take the form of, for example, tablets or capsules.

Provided herein are also kits that include at least one HDAC inhibitor compound described herein, or a pharmaceutically acceptable salt, prodrug, or solvate thereof, and suitable packaging. In one embodiment, a kit further includes instructions for use. In one embodiment, a kit includes at least one HDAC inhibitor compound or a pharmaceutically acceptable salt, prodrug, or solvate thereof, and a label and/or instructions for use of the compounds in treatment of the indications, including the diseases or disorders described herein.

Provided herein are also articles of manufacture that include at least one HDAC inhibitor compound described herein, or a pharmaceutically acceptable salt, prodrug, or solvate thereof, in a suitable container. The container may be a vial, jar, ampoule, preloaded syringe, and intravenous bag.

Methods of Identifying HDAC Inhibitor Compounds

Provided are also methods of identifying compounds that are HDAC inhibitors, suitable for treating the diseases or disorders described herein. In certain variations, provided herein are methods of identifying odorant compounds that are HDAC inhibitors. In some variations, provided herein are methods of identifying volatile compounds that are HDAC inhibitors. In one variation, provided herein is a method of identifying volatile HDAC inhibitors using *Drosophila* or cells.

The HDAC inhibitor compounds may be identified through cheminformatics approaches. In some embodiments, the HDAC inhibitor compounds are identifying by analyzing a known HDAC inhibitor compound to develop molecular descriptors of the known compound, and using those molecular descriptors to screen putative compounds for structural similarity. Through such methods, HDAC inhibitor compounds, including odorant compounds and volatile compounds, may be identified which were previously unknown.

Enumerated Embodiments

The following enumerated embodiments are representative of some aspects of the invention.
1. A method of treating, or delaying the development of, a disease or disorder in a subject in need thereof, comprising administering to the subject an effective amount of a histone deacetylase (HDAC) inhibitor compound.
2. The method of embodiment 1, wherein the disease or disorder is responsive to the inhibition of HDAC.
3. The method of embodiment 1 or 2, wherein the disease or disorder is a neurological disorder, cancer, chronic obstructive pulmonary disorder (COPD), or an infectious disease.
4. The method of embodiment 3, wherein the neurological disorder is Huntington's disease, Alzheimer's disease, Parkinson's disease, multiple sclerosis, or dementia.
5. A method of treating, or delaying the development of, neurodegeneration in a subject in need thereof, comprising administering to the subject an effective amount of a histone deacetylase (HDAC) inhibitor compound to treat neurodegeneration in the subject.
6. A method of modulating gene expression in neurons in a subject in need thereof, comprising administering to the subject an effective amount of a histone deacetylase (HDAC) inhibitor compound to modulate gene expression in the neurons of the subject.

7. A method of improving immune response in a subject in need thereof, comprising administering to the subject an effective amount of a histone deacetylase (HDAC) inhibitor compound to improve the immune response of the subject.

8. A method of inhibiting histone deacetylase (HDAC) in a subject in need thereof, comprising administering the subject an effective amount of a HDAC inhibitor compound to inhibit HDAC in the subject.

9. The method of any one of embodiments 1 to 8, wherein the subject is a mammal.

10. The method of any one of embodiments 1 to 8, wherein the subject is a human.

11. The method of any one of embodiments 1 to 10, wherein the HDAC inhibitor compound is a volatile compound, or a volatile inhaled compound.

12. The method of any one of embodiments 1 to 10, wherein the HDAC inhibitor compound is an odorant or tastant.

13. The method of any one of embodiments 1 to 12, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, acetic acid, propionic acid, 2,3-pentanedione, 2-butanone, diacetyl, or any combinations thereof.

14. The method of any one of embodiments 1 to 12, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, or diacetyl, or any combinations thereof.

15. The method of any one of embodiments 1 to 12, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, or propyl propionate, or any combinations thereof.

16. The method of any one of embodiments 1 to 12, wherein the HDAC inhibitor compound is diacetyl.

17. The method of any one of embodiments 1 to 16, wherein the HDAC inhibitor compound is nasally or orally administered.

18. The method of any one of embodiments 1 to 16, wherein the HDAC inhibitor compound is administered to the subject as a gas or vapor.

19. A pharmaceutical composition comprising:
a histone deacetylase (MAC) inhibitor compound; and
at least one pharmaceutically acceptable excipient.

20. The pharmaceutical composition of embodiment 19, wherein the HDAC inhibitor compound is a volatile compound, or a volatile inhaled compound.

21. The pharmaceutical composition of embodiment 19 or 20, wherein the HDAC inhibitor compound is an odorant or tastant.

22. The pharmaceutical composition of any one of embodiments 19 to 21, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, acetic acid, propionic acid, 2,3-pentanedione, 2-butanone, diacetyl, or any combinations thereof.

23. The pharmaceutical composition of any one of embodiments 19 to 21, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, or diacetyl, or any combinations thereof.

24. The pharmaceutical composition of any one of embodiments 19 to 21, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, or propyl propionate, or any combinations thereof.

25. The pharmaceutical composition of any one of embodiments 19 to 21, wherein the HDAC inhibitor compound is diacetyl.

26. The pharmaceutical composition of any one of embodiments 19 to 25, wherein the HDAC inhibitor compound is present in the pharmaceutical composition in an amount between 1%-5%; 6%-10%; 11-30%; 31%-50%; 50%-100% (volume/volume or weight/volume).

27. A kit, comprising a histone deacetylase (HDAC) inhibitor compound, and suitable packaging.

28. A kit, comprising a histone deacetylase (HDAC) inhibitor compound; and a label and/or instructions for use of the compound in treatment of a neurological disorder, cancer, chronic obstructive pulmonary disorder (COPD), or an infectious disease.

29. The kit of embodiment 28, wherein the neurological disorder is Huntington's disease, Alzheimer's disease, Parkinson's disease, multiple sclerosis, or dementia.

30. A kit, comprising a histone deacetylase (HDAC) inhibitor compound; and a label and/or instructions for use of the compound in treatment of a disease or disorder responsive to the inhibition of HDAC.

31. The kit of any one of embodiments 27 to 30, wherein the HDAC inhibitor compound is a volatile compound, or a volatile inhaled compound.

32. The kit of any one of embodiments 27 to 30, wherein the HDAC inhibitor compound is an odorant or tastant.

33. The kit of any one of embodiments 27 to 32, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, acetic acid, propionic acid, 2,3-pentanedione, 2-butanone, diacetyl, or any combinations thereof.

34. The kit of any one of embodiments 27 to 32, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, or diacetyl, or any combinations thereof.

35. The kit of any one of embodiments 27 to 32, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, or propyl propionate, or any combinations thereof.

36. The kit of any one of embodiments 27 to 32, wherein the HDAC inhibitor compound is diacetyl.

37. An article of manufacture, wherein the article of manufacture comprises an odorant or tastant histone deacetylase (HDAC) inhibitor compound, in a suitable container.

38. The article of manufacture of embodiment 37, wherein the container is a vial, jar, ampoule, preloaded syringe, and intravenous bag.

39. The article of manufacture of embodiment 37 or 38, wherein the HDAC inhibitor compound is a volatile compound, or a volatile inhaled compound.

40. The article of manufacture of any one of embodiments 37 to 39, wherein the HDAC inhibitor compound is an odorant or tastant.

41. The article of manufacture of any one of embodiments 37 to 39, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, acetic acid, propionic acid, 2,3-pentanedione, 2-butanone, diacetyl, or any combinations thereof.

42. The article of manufacture of any one of embodiments 37 to 39, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, propyl propionate, or diacetyl, or any combinations thereof.

43. The article of manufacture of any one of embodiments 37 to 39, wherein the HDAC inhibitor compound is 2-methyl-2-propenal, methyl vinyl ether, methyl formate, 1,4-pentadien-3-one, furfural, dimethyl carbonate, methyl dimethyl acrylate, methyl acrylate, methyl methacrylate, isobutyl formate, isoamyl formate, gamma-valerolactone, propylene carbonate, methyl butyrate, 2-pentanone, propylene acetal, isobutyl acetate, 2,3-butane diol, 3-methyl-3-buten-2-one, allyl acetone, 4-methyl-3-penten-2-one, mesityl oxide, isopropyl 2-propenoate, gamma-butyrolactone, 3-hydroxybutanoic acid lactone, 2-methyl-1-penten-3-one, or propyl propionate, or any combinations thereof.

44. The article of manufacture of any one of embodiments 37 to 39, wherein the HDAC inhibitor compound is diacetyl.

EXAMPLES

The following Examples are merely illustrative and are not meant to limit any aspects of the present disclosure in any way.

Example 1

Effect of Diacetyl Exposure on RNA Expression in *Drosophila* Antenna

For five days, *Drosophila* were exposed to 1% diacetyl (odor 1) on filter paper; fed known HDAC inhibitor sodium butyrate (Na-but; 10 mM); or fed known HDAC inhibitor valproic acid (10 mM). Genes expression in the antenna of the *Drosophila* were then analyzed, and showed that exposure to odor1 (diacetyl) resulted in increases in expression of some genes in the antenna (FIG. 1A). Gene expression in the antenna were evaluated through whole mount RNA in situ analysis of adult *Drosophila* antenna Gr63a, and showed over-expression in flied exposed to odor 1 and fed sodium butyrate, as compared to flies that were untreated or had mock exposure (FIG. 1A).

Figure 1B:
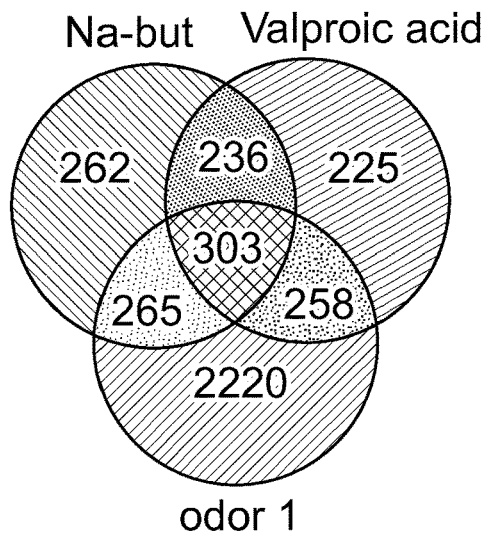
FIG. 1B depicts the overlap of genes upregulated in *Drosophila* antennal RNA-Seq following 5 day exposure of sodium butyrate (Na-but), valproic acid, and odor 1 (diacetyl).

RNA sequencing of the *Drosophila* antenna showed overlap between which genes were up-regulated in the odor1-treated *Drosophila* and the *Drosophila* treated with sodium and valproic acid (FIG. 1B).

Example 2

Effect of Diacetyl on Human HDAC1

Figure 1C:
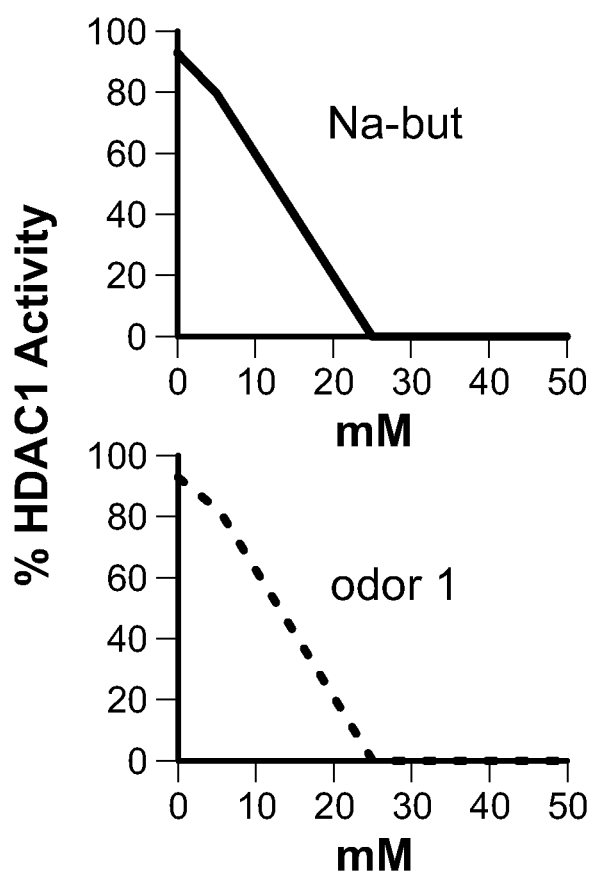
FIG. 1C depicts two graphs showing human HDAC1 in vitro activity measurements of inhibition curves for sodium butyrate (Na-but; top) at 10 mM compared to odor 1 (diacetyl; bottom).

The ability of diacetyl (odor 1) to inhibit human HDAC activity was investigated using in-vitro assays with a human HDAC1 kit. This demonstrated that odor1 is an effective HDAC inhibitor and comparable to sodium butyrate (FIG. 1C).

Figure 1D:
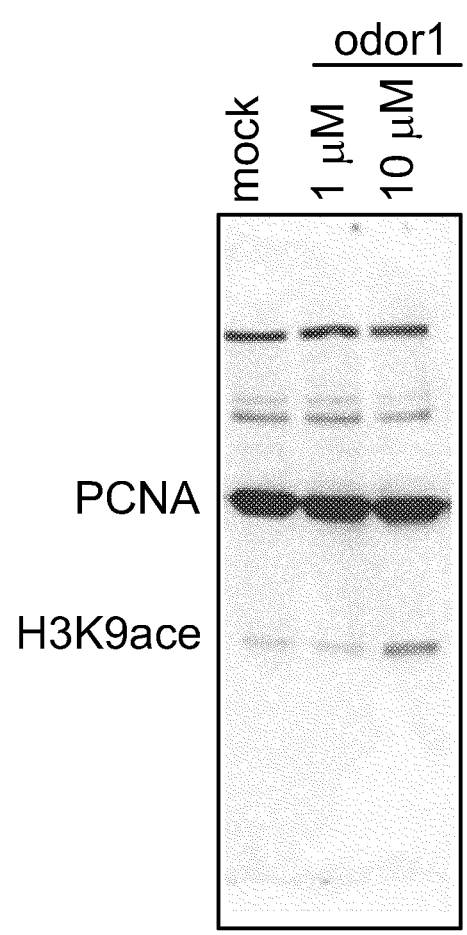
FIG. 1D depicts a gel chromatograph analysis of histone 3K9 acetylation (H3K9ace; 17 kDa) in HEK cells exposed to odor 1 (diacetyl). Proliferating cell nuclear antigen (PCNA) is a 29 kDa nuclear protein used as a loading control of nuclear protein extracts.

The effect of diacetyl on histone acetylation was further investigated using direct analysis of histone 3K9 acetylation in HEK cells. In vivo activity of diacetyl was determined by gel electrophoresis chromatography of HEK cell lysate exposed to 0 µM, 1 µM and 10 µM of diacetyl (odor 1) in whole HEK cell lysates. As shown in FIG. 1D, the level of acetyl H3K9 (H3K9Ace; 17 kDa) increased with increasing concentrations of diacetyl. Proliferating cell nuclear antigen (PCNA; 29 kDa) is a nuclear protein included as a loading control for nuclear protein extracts.

Example 3

Effect of Diacetyl on Huntington's Model *Drosophila*

It has previously been shown that administration through food of some HDAC inhibitors, such as SAHA (suberoylanilide hydroxamic acid) and sodium butyrate, can slow down degeneration of photoreceptor cells (rhabdomeres) in a *Drosophila* model for Huntington's disease expressing the human protein with an expanded polyglutamine repeat.

Figure 2A:
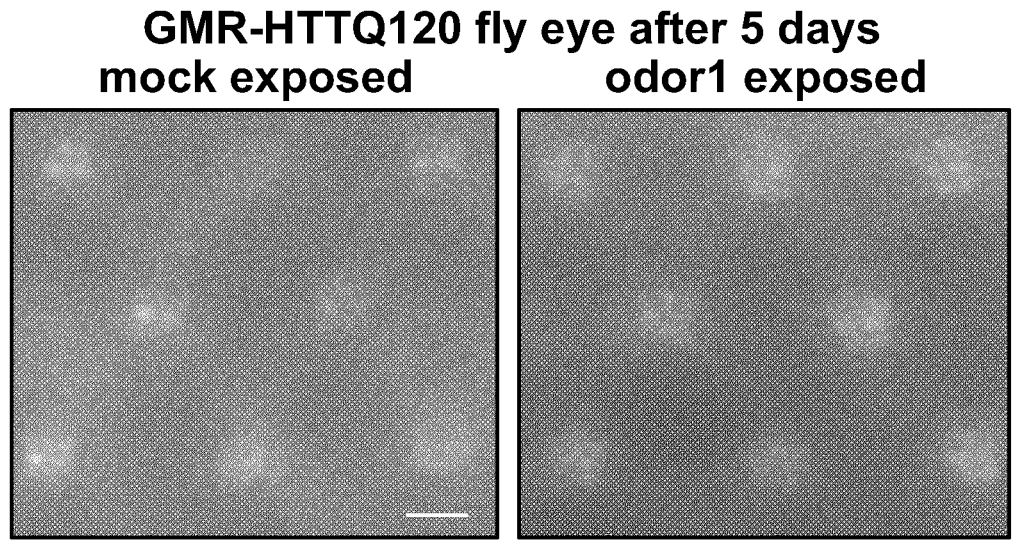
FIG. 2A depicts images of the omatidia in the eye of 5 day old *Drosophila* expressing human Huntington HTTQ120 protein from a GMR promoter, without exposure to odor 1 (diacetyl; left) and with exposure to odor 1 (right).
Figure 2B:
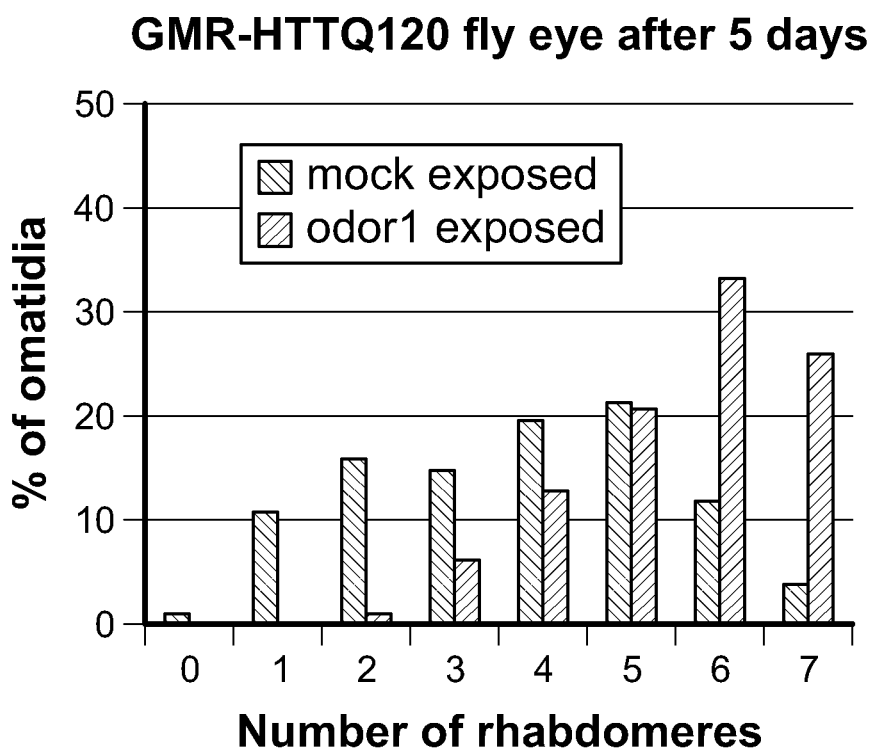
FIG. 2B is a chart showing the number of rhabdomerees visible in the omatidia in the eye of 5 day old *Drosophila* expressing human Huntington HTTQ120 protein from a GMR promoter, with and without exposure to odor 1 (diacetyl).

To investigate the effect of diacetyl on neurodegeneration, Huntington model *Drosophila* flies (GMR-HTTQ120; expressing human huntington HTTQ120 protein from a GMR promoter) were exposed to odor 1 (diacetyl) at 1% concentration from filter paper for five days as a volatile scent. Following exposure, the omatidia in the eyes of the flies were visualized. As shown in FIG. 2A, flies exposed to odor 1 (right image) had greater rhabdomeres in their omatidia as compared to flies which were not exposed to odor 1 (left), indicating exposure to odor 1 reduced neurodegeneration in the Huntington's disease model *Drosophila*. The number of rhabdomeres present in the omatidia were counted (wildtype flies have 7 rhabdomeres in each omatidia). As shown in FIG. 2B, flies exposed of odor 1 had a greater percentage of omatidia with a higher number of rhabdomeres than flies which were not exposed to odor 1 (mock exposed).

Example 4

Screening for HDAC Inhibitors

Cheminformatics was used to screen in-silica >400,000 volatile compounds (including 12,000 natural compounds) based on structural similarity to diacetyl. This screen identified volatile compounds that target HDAC, as summarized in Table 1 below.

TABLE 1

| No. | Compound structures/ SMILES | CAS number | Compound Name | Values for Structural Similarity to Diacetyl |
|---|---|---|---|---|
| 1 | 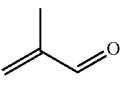<br>C=C(C)C=O | 78-85-3 | 2-methyl-2-propenal | 75.2998269 |
| 2 | 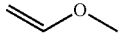<br>C=COC | 107-25-5 | methyl vinyl ether | 71.3919862 |
| 3 | 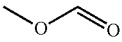<br>COC=O | 107-31-3 | methyl formate | 65.0662747 |
| 4 | 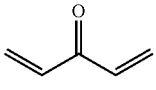<br>C=CC(C=C)=O | 1890-28-4 | 1,4-pentadien-3-one | 62.2838515 |
| 5 | 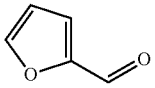<br>C1=C(OC=C1)C=O | 98-01-1 | furfural | 60.9090668 |
| 6 | 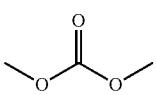<br>O=C(OC)OC | 616-38-6 | dimethyl carbonate | 58.7865278 |

TABLE 1-continued

| No. | Compound structures/ SMILES | CAS number | Compound Name | Values for Structural Similarity to Diacetyl |
|---|---|---|---|---|
| 7 | 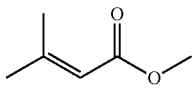<br>CC(=CC(OC)=O)C | 924-50-5 | methyl dimethyl acrylate | 56.4374599 |
| 8 | 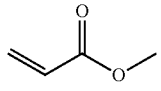<br>COC(C=C)=O | 96-33-3 | methyl acrylate | 54.4834458 |
| 9 | 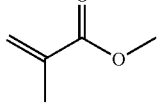<br>CC(C(OC)=O)=C | 80-62-6 | methyl methacrylate | 52.9656561 |
| 10 | 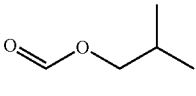<br>C(C(C)C)OC=O | 542-55-2 | isobutyl formate | 51.695869 |
| 11 | 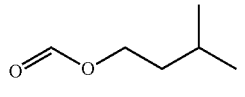<br>C(COC=O)C(C)C | 110-45-2 | isoamyl formate | 51.6363523 |
| 12 | 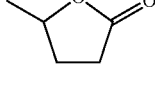<br>CC1OC(CC1)=O | 108-29-2 | gamma-valerolactone | 50.7047376 |
| 13 | 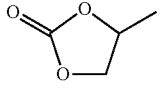<br>O=C(O1)OCC1C | 108-32-7 | propylene carbonate | 48.2517827 |
| 14 | 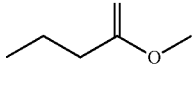<br>C(C(OC)=O)CC | 623-42-7 | methyl butyrate | 47.8320457 |
| 15 | 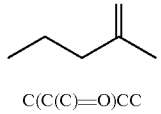<br>C(C(C)=O)CC | 107-87-9 | 2-pentanone | 47.0857645 |
| 16 | 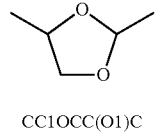<br>CC1OCC(O1)C | 3390-12-3 | propylene acetal | 46.8670948 |

TABLE 1-continued

| No. | Compound structures/ SMILES | CAS number | Compound Name | Values for Structural Similarity to Diacetyl |
|---|---|---|---|---|
| 17 | 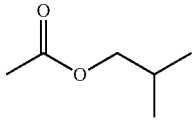<br>C(OC(C)=O)C(C)C | 110-19-0 | isobutyl acetate | 46.8552005 |
| 18 | 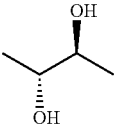<br>[C@H](O)([C@@H](O)C)C | 513-85-9 | 2,3-butane diol | 46.6523648 |
| 19 | 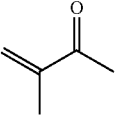<br>CC(C(=C)C)=O | 814-78-8 | 3-methyl-3-buten-2-one | 43.6858474 |
| 20 | 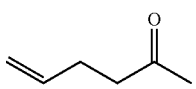<br>C(C(C)=O)CC=C | 109-49-9 | allyl acetone | 43.6091591 |
| 21 | 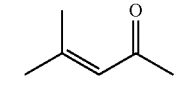<br>O=C(\C=C(/C)C)C | Training Odor | 4-methyl-3-penten-2-one | 43.4182201 |
| 22 | 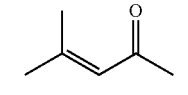<br>CC(C)=CC(C)=O | 141-79-7 | mesityl oxide | 41.9427793 |
| 23 | 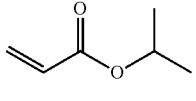<br>C=CC(OC(C)C)=O | 689-12-3 | isopropyl 2-propenoate | 41.8439313 |
| 24 | 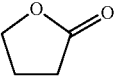<br>O=C1CCCO1 | 96-48-0 | gamma-butyrolactone | 41.6943859 |
| 25 | 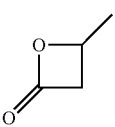<br>CC1CC(O1)=O | 36536-46-6 | 3-hydroxybutanoic acid lactone | 41.6249406 |

TABLE 1-continued

| No. | Compound structures/ SMILES | CAS number | Compound Name | Values for Structural Similarity to Diacetyl |
|---|---|---|---|---|
| 26 | 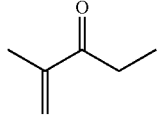<br>C=C(C)C(CC)=O | 25044-01-3 | 2-methyl-1-penten-3-one | 41.2767404 |
| 27 | 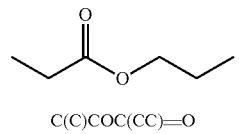<br>C(C)COC(CC)=O | 106-36-5 | propyl propionate | 41.0651088 |

Example 5

Diacetyl Volatiles Regulate Global Gene Expression

Figure 3A:
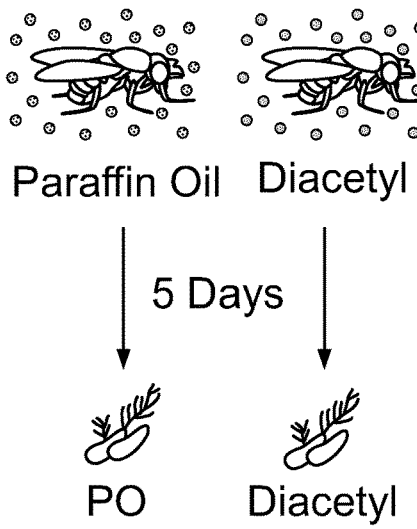
FIGS. 3A-3F demonstrate that exposure to a natural odorant alters gene expression in the antenna.

In order to examine the physiological effects of long-term exposure to an odorant, flies were maintained in vials with circulating volatiles from headspace of a low concentration (1% in paraffin oil) of the odorant diacetyl, which acts on a number of different receptor pathways in Drosophila. In a similar manner to previous odor-exposure studies, flies were exposed to diacetyl for 5 days and performed an RNA-seq analysis of the antennae, which are known odor-detecting organs. The transcriptome was compared with a control group of age-matched flies that were exposed to the headspace of the solvent paraffin oil (PO, FIG. 3A).

Figure 3B:
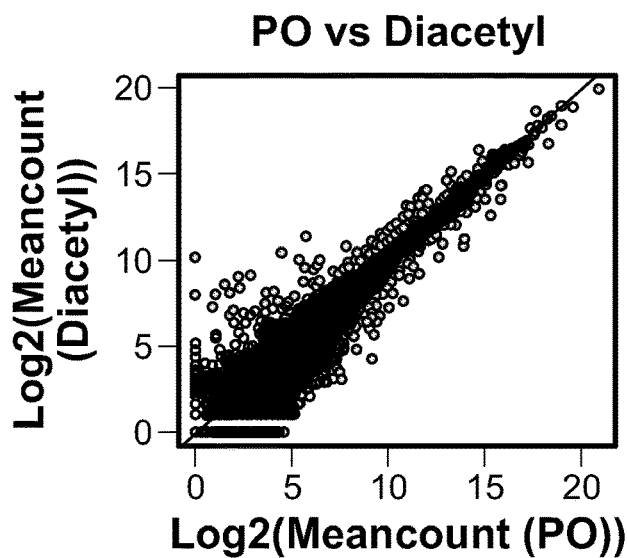
Figure 3C:
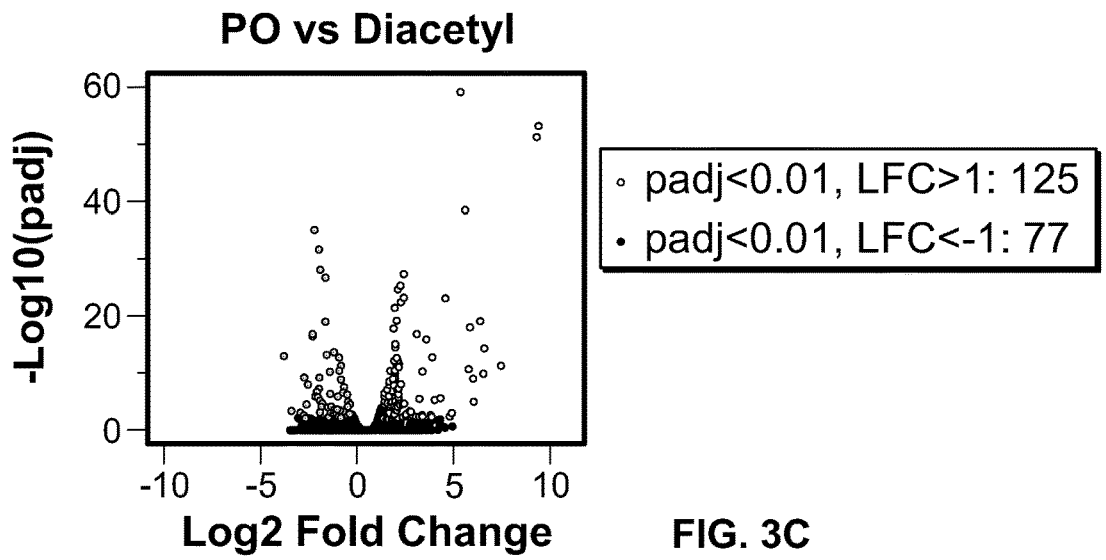

Surprisingly, the antennal transcriptional profile of diacetyl-exposed flies showed substantial changes in gene expression when compared to the solvent control (FIG. 3B). 202 differentially-expressed genes (DEGs) ($p<0.01$) were identified in the antennal transcriptome of diacetyl-exposed flies compared to control animals (red dots in FIG. 3B). 125 genes were significantly up-regulated >2-fold (log 2 fold-change >1; red dots on the right in FIG. 3C) and 77 genes were significantly down-regulated >2-fold (log 2 fold-change <−1; blue dots on the left in FIG. 3C) in diacetyl-exposed flies. This observation suggests that nearly 1.5% of genes in the Drosophila genome are affected by exposure to this volatile chemical.

Figure 3D:
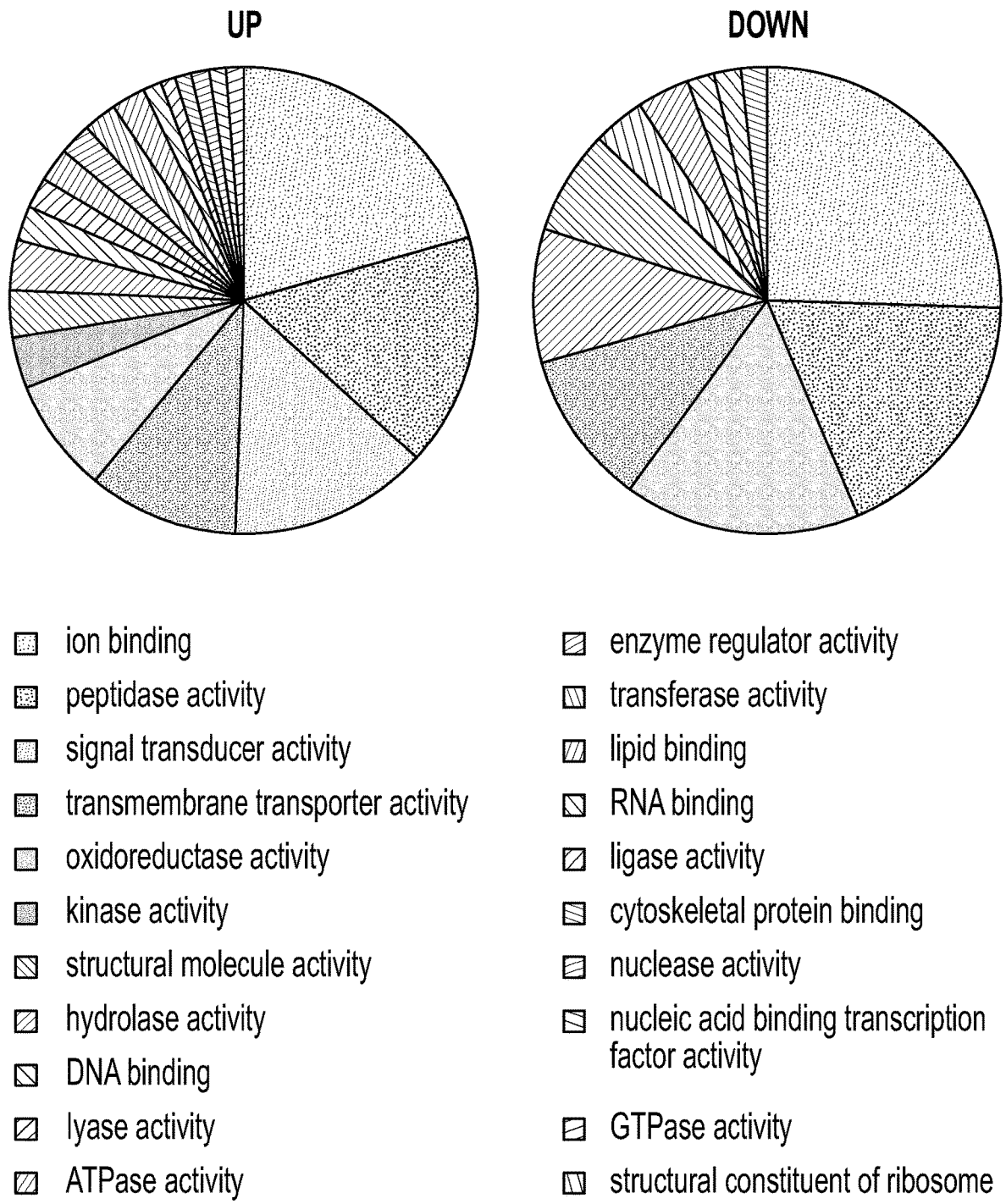

In order to understand what types of genes were being regulated by his unusual phenomenon, a Gene Ontology (GO) analysis (FIG. 3D) was performed. The molecular functions of the upregulated genes were diverse: 18 genes were assigned "ion binding," 14 "peptidase activity," 12 "signal transducer activity," 9 "transmembrane transporter activity," 7 "oxidoreductase activity," and the rest distributed across other classes. A smaller fraction of the down-regulated genes were also widely distributed, with 14 genes assigned "ion binding," 10 "peptidase activity," 9 "oxidoreductase activity," 6 "transmembrane transporter activity," 5 "hydrolase activity," and the rest distributed across other classes. In order to examine if a particular GO term of up- or down-regulated genes is overrepresented among the odor-regulated genes, a GO enrichment analysis was performed.

Figure 3E:
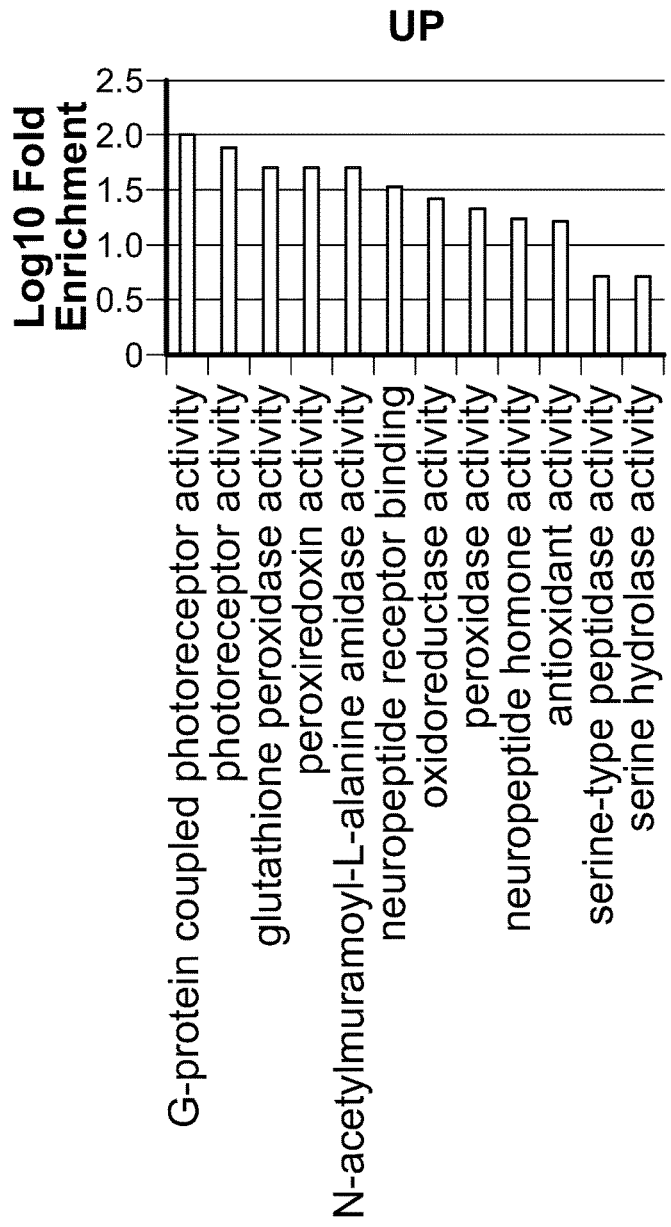
Figure 3F:
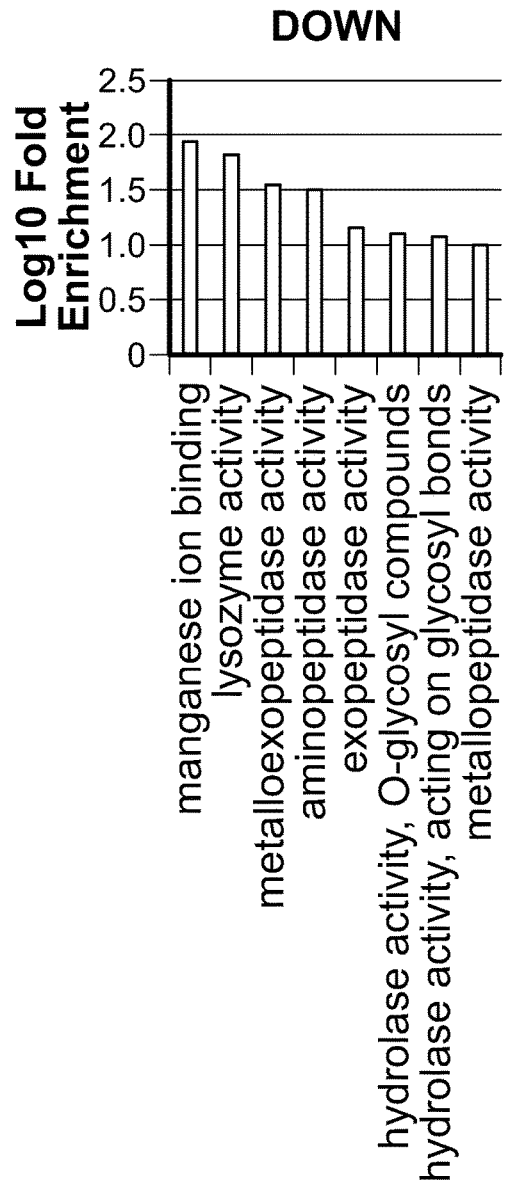
Figure 4A:
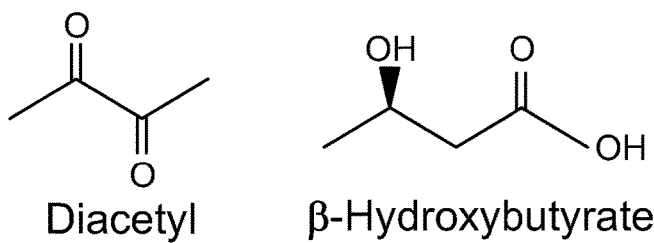
FIGS. 4A-4E demonstrate that diacetyl acts as a Histone Deacytylase inhibitor in vitro.
Figure 4B:
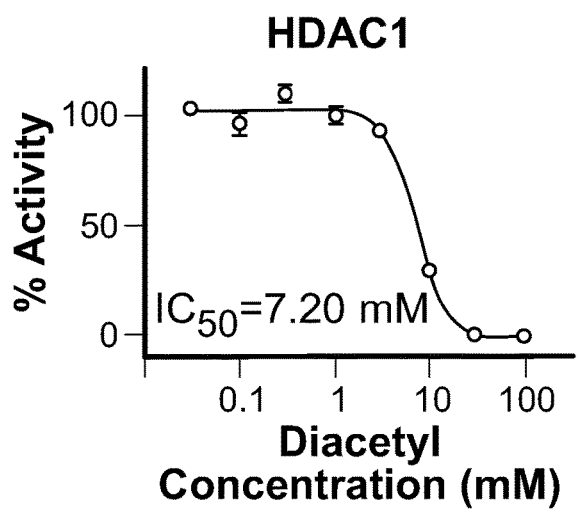
Figure 4C:
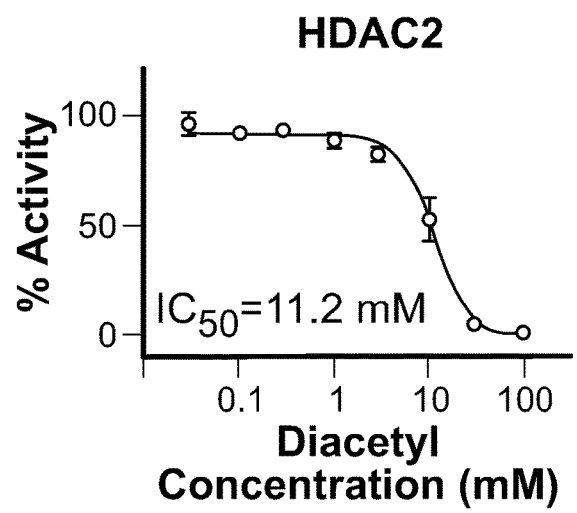
Figure 4D:
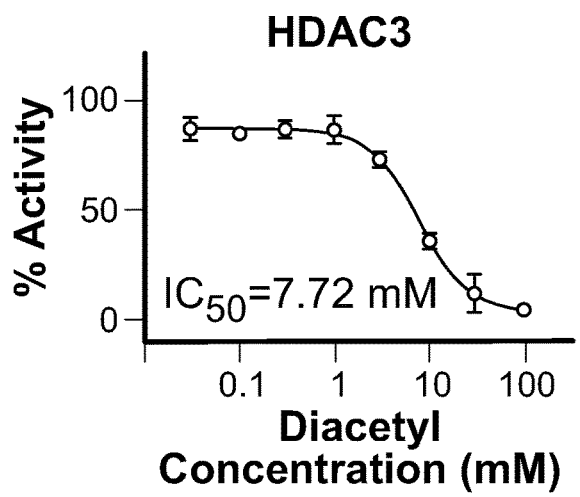
Figure 4E:
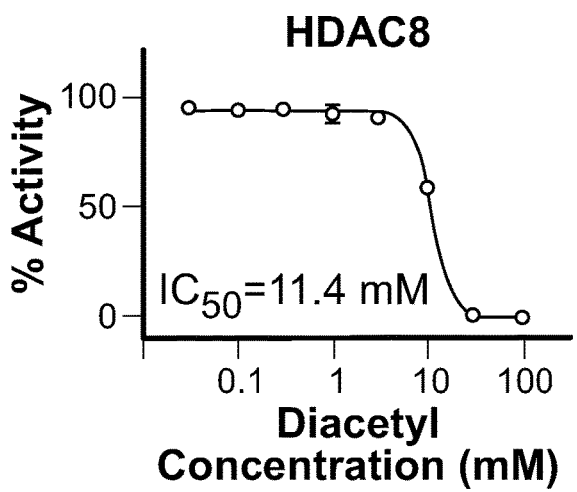

Interestingly, several GO terms were significantly enriched in the up-regulated gene list: 100-fold enrichment of "G-protein coupled photoreceptor activity" $p<10^{-7}$) and ~80-fold enrichment of "photoreceptor activity" ($p<10^{-8}$) are related to visual system function (FIG. 3E). GO terms that were between 5-50 times enriched ($p<$~0.05) such as "glutathione peroxidase activity" and "peroxiredoxin activity" (FIG. 3E) were found. Several enzyme activity-related GO-terms were significantly enriched as well in the down-regulated gene list, such as "manganese ion binding," "lysozyme activity," "metalloexopeptidase activity," "aminopeptidase activity," and "exopeptidase activity" (FIG. 3F). Surprisingly, GO terms related to odor detection such as "sensory detection of chemical stimulus," "chemosensory perception," and "neurological system process" were not enriched. The differentially-expressed genes are distributed on different chromosome arms, suggesting that diacetyl exposure modulates gene expression across the genome and hinting at a global mechanism of action.

Drosophila Stocks and Manipulations

Fly stocks were maintained on conventional fly food under a 12 hr light:12 hr dark cycle at 18° C. or 25° C. Unless otherwise indicated, w1118 backcrossed 5 times to Canton-S (wCS) was used as a wild-type control in most of the experiments. The transgenic line pGMR-HTTQ120 was obtained from the Bloomington stock center (BDSC #8533).

Odor Exposure Protocol for Transcriptome Analysis

Flies were exposed to diacetyl (2,3-Butanedione, B85307, Sigma-Aldrich, St. Louis, Mo.) by placing them in vials in a cylindrical closed container (112 mm diameter×151 mm height) along with an odor-containing glass vial. The odorant was dissolved in 10 mL paraffin oil at 1% dilution. For a given exposure protocol, two groups of flies were prepared: those exposed to 1% diacetyl headspace and those exposed to paraffin oil headspace alone (control flies). Adult male flies aged 1 d were transferred to fly vials containing fresh medium, and put into the container with the odor vial. At the end of the fifth day of exposure, flies were collected, and their antennae were dissected for RNA extraction. All treatments and experiments were performed at room temperature. For the recovery experiment, flies were transferred again to the container containing a glass vial of paraffin oil after 5 days of diacetyl exposure. At the end of the fifth day of recovery, flies were collected, and their antennae were dissected for RNA extraction.

HDAC Inhibitor Treatment Protocol for Transcriptome Analysis

Sodium butyrate (B5887, Sigma-Aldrich) or valproic acid (P4543, Sigma-Aldrich) were dissolved in normal fly food medium at the final concentration of 10 mM. Three groups of flies were prepared: those treated with one of the HDAC inhibitors and those without HDAC inhibitor treatment (control flies). Adult flies aged 1 d were transferred to fly vials containing medium with or without a HDAC inhibitor. At the end of the fifth day of treatment, flies were collected, and their antennae were dissected for RNA extraction. All treatments and experiments were performed at room temperature.

RNA Isolation and Sequencing

The second and third antennal segments from 40-60 male flies after treatment were carefully hand-dissected from the head, collected in 1.5 ml microfuge tubes kept cold in liquid nitrogen. Antennae were mechanically crushed with disposable RNAse-free plastic pestles, and total RNA was isolated using a Trizol-based protocol. cDNA libraries were prepared from total RNA (300-1000 ng/sample) using the Illumina TruSeq RNA Library Preparation Kit (Illumina Catalog #RS-122-2001). Samples were submitted to the UCR IIGB sequencing core for high-throughput sequencing using the Illumina HiSeq2500 platform. Raw reads were aligned to the *Drosophila melanogaster* reference genome (dmel-all-chromosome-r5.48.fasta) with Tophat2, and a count table of reads overlapping with exonic regions of genes was generated by the UCR bioinformatics core. The numbers of biological replicates are: 2, day 5 paraffin oil; 1, day 5 diacetyl; 2, day 5 mock; 2, day 5 sodium butyrate; 2, day 5 valproic acid; 2, day 10 paraffin oil recovery; 2, day 10 diacetyl recovery.

The read count table for all the genes were then imported into R and a statistical analysis of differential gene expression using the DESeq package (1.22.0) was performed. Genes were considered to be differentially-expressed if they had a padj<0.01 and log 2 fold-change >1 or <−1, both based on the DEseq normalized samples. The gene list analysis was performed using the GO Term Mapper (http://go.princeton.edu/) with Generic GO slim datasets, and the Statistical overrepresentation test was performed using the PANTHER classification (http://www.pantherdb.org/) system with GO complete datasets.

Example 6

Diacetyl Acts as a Histone Deacetylase Inhibitor In Vitro

In order to directly test whether diacetyl acts as an inhibitor of HDACs, in vitro acetylation assays was performed with purified human HDACs. In this example, β-hydroxybutyrate (a naturally-occurring HDAC inhibitor secreted by the liver, targeting zinc-dependent HDACs) was used for comparison.

In this example, diacetyl was found to inhibit all 4 purified human Class I HDACs (HDAC1, 2, 3 and 8). The inhibition occurred in a dose-dependent manner in the in vitro assay, albeit to slightly different extents. The $IC_{50}$ values for HDAC1, 2, 3 and 8 were 7.20 mM, 11.2 mM, 7.72 mM and 11.4 mM, respectively (FIGS. 4B-4E). These values for HDAC inhibition are comparable to those of β-hydroxybutyrate.

In mammals, β-hydroxybutyrate has been shown to be an endogenous histone deacetylase inhibitor. Up-regulation of circulating β-hydroxybutyrate during fasting or calorie restriction induces changes in the expression of a set of genes including those involved in protective activities against oxidative stress. Oxidative stress is thought to be involved in several types of diseases, especially in aging-related diseases including Alzheimer's and Parkinson's diseases, and β-hydroxybutyrate have been shown to prevent neurodegeneration in disease model animals. The HDAC class selectivity and IC50s of β-hydroxybutyrate are similar to that of diacetyl (FIG. 4). It is contemplated that exposure to diacetyl can also modulate the gene sets involved in oxidative stress resistance in the brain and induce protective effects against these neurodegenerative diseases.

HDAC Activity Assays

HDAC activity of class I HDACs (HDAC1, 2, 3 and 8) was measured with the fluorometric HDAC Activity Assay kit: HDAC1 (10011563, Cayman Chemical, Ann Arbor, Mich.), HDAC2, HDAC 3 and HDAC 8 (50062, 50073 and 50068, BPS Bioscience, San Diego, Calif.), according to the manufacturer's instructions.

Example 7

Diacetyl Acts as a Histone Deacetylase Inhibitor In Vitro

In order to test whether diacetyl can increase acetylation of histones in vivo, human HEK293 cells were used, which offer a tractable system to prepare nuclear extracts. The cells were exposed to different doses of diacetyl for 2 or 6 hours, and monitored histone acetylation levels by Western blot analysis from nuclear extract. Compared to the mock treatment, 10 mM diacetyl significantly increased H3K9 acetylation level even within 2 hours of treatment (FIG. 5A). The acetylation levels of H3K14 and H4K5 were not affected (FIG. 5A). As expected, after 6 hours of treatment the H3K9 acetylation induced by 10 mM diacetyl was further increased, while the acetylation levels of H3K14 and H4K5 were unaffected (FIG. 5B). Treatment with a lower 1 mM dosage of diacetyl did not alter the acetylation levels of H3K9, H3K14 or H4K5, suggesting dosage dependence (FIGS. 5A-5B).

Animals are typically exposed to odorants and tastants in their food over prolonged periods of time. In order to test the effect of a lower exposure that could be naturally relevant, a 5-day exposure time at a 100-fold lower concentration was selected, comparable to amounts found in certain foods. Remarkably, when HEK293 cells were treated with this lower dose of diacetyl (100 μM), H3K9 acetylation level increased only after 96 hrs of exposure and reached significantly higher levels after 120 hrs. These results demonstrate that prolonged exposure to even low levels of diacetyl can greatly impact the epigenetic environment inside the cell. More importantly, even a 5-day exposure was sufficient to alter the epigenetic state of cells at concentrations that are present in some food sources (~10 ppm). Taken together, these results demonstrate that diacetyl is an HDAC inhibitor that can cause global modulation of gene expression, histone acetylation in cells, and inhibition of purified HDAC enzymes.

Diacetyl was shown to modulate acetylation levels of histones to influence epigenetic state in a dose- and time-dependent manner. Importantly, dosages of diacetyl consistent with concentrations in some wine and dairy products can influence epigenetic state with long-term treatment (FIGS. 5C and 5D). Moreover, the headspace of 1% diacetyl slows the progression of a type of neurodegeneration in Huntington's model flies.

Cell Culture and Treatment

Human embryonic kidney 293 (HEK293) cells were grown in 100 mm cell culture dishes with Dulbecco's modified Eagle's medium (DMEM) (10-013, Corning, Manassas, Va.), supplemented with 10% fetal bovine serum (FBS) (26140-079, Gibco, Carlsbad, Calif.) at 37° C. with 5% $CO_2$. Cells that were ~80% confluent were treated with freshly-prepared medium supplemented with diacetyl at concentrations indicated. In order to prevent diffusion of diacetyl odor from the treatment dishes to the outside environment, the cell culture dishes were put into a custom-made container (155.6×155.6×85.7 mm) with a charcoal filter top. The cells for non-treatment controls were handled in the same manner without adding diacetyl to the medium.

Preparation of Nuclear Extracts from HEK293 Cells

Nuclear extracts of HEK293 cells were prepared according to a protocol described previously (Andrews and Faller, 1991), with minor modifications. In brief, HEK293 cells were washed twice with cold phosphate-buffered saline (PBS) and lysed with hypotonic buffer (10 mM HEPES-KOH [pH 7.9], 1.5 mM $MgCl_2$, 10 mM KCl, protease inhibitor cocktail [Roche], 1 mM DTT, 1 mM TSA). Following a brief centrifugation, the pellet was resuspended in hypertonic buffer (20 mM HEPES-KOH [pH 7.9], 25% glycerol, 420 mM NaCl 1.5 mM $MgCl_2$, 0.2 mM EDTA, protease inhibitor cocktail (04693159001, Roche, Indianapolis, Ind.), 1 mM DTT, 1 mM TSA). The supernatant was recovered as nuclear extract.

Western Blot Analysis

Proteins in the nuclear extracts (60 μg protein) were separated by SDS-PAGE gels (456-1043, Bio-Rad, Hercules, Calif.), transferred onto PVDF membranes (162-0174, Bio-Rad), and incubated with anti-histone antibodies: acetylated H3K9 (1/2000: ab4441, abeam, Cambridge, Mass.), acetylated H3K14 (1/5000: 06-911, EMD Millipore, Billerica, Mass.), acetylated H4K5 (1/2000: 07-327, EMD Millipore). Bound antibody was detected by horseradish peroxidase-conjugated anti-rabbit secondary antibody (1/20000: 1705046, Bio-Rad) and developed using Clarity™ Western ECL Substrate (1705060, Bio-Rad). Signals were detected and captured by ImageQuant™ LAS 4000 mini (GE healthcare, Pittsburgh, Pa.), and band intensities were quantified with ImageJ software. H3K9 acetylation intensity in individual lanes was reported relative to the normalized Mock treatment (Mock H3K9ace/Mock PCNA), and calculated using this formula: Relative H3K9ace intensity for each timepoint=(Diacetyl H3K9ace/diacetyl PCNA)/(Mock H3K9ace/Mock PCNA).

Example 8

Figure 6A:
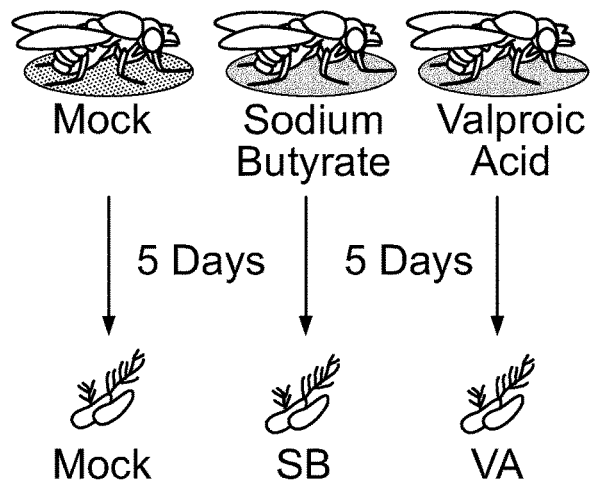
FIGS. 6A-6I demonstrate that Gene modulatory profile for diacetyl differs from known HDAC inhibitors.

Diacetyl-Modulated Genes Show Partial Overlap with those Modulated by Known HDAC Inhibitors This example investigates the overlap among genes modulated by diacetyl as compared to sodium butyrate and valproic acid, which are known HDAC inhibitors. Using the *Drosophila* antennae, we performed transcriptome analysis after raising the flies on food containing sodium butyrate (SB), valproic acid (VA), or untreated food for 5 days (FIG. 6A). We next compared the differentially-regulated gene profiles following each treatment to the one induced by exposure to volatile diacetyl.

Figure 6B:
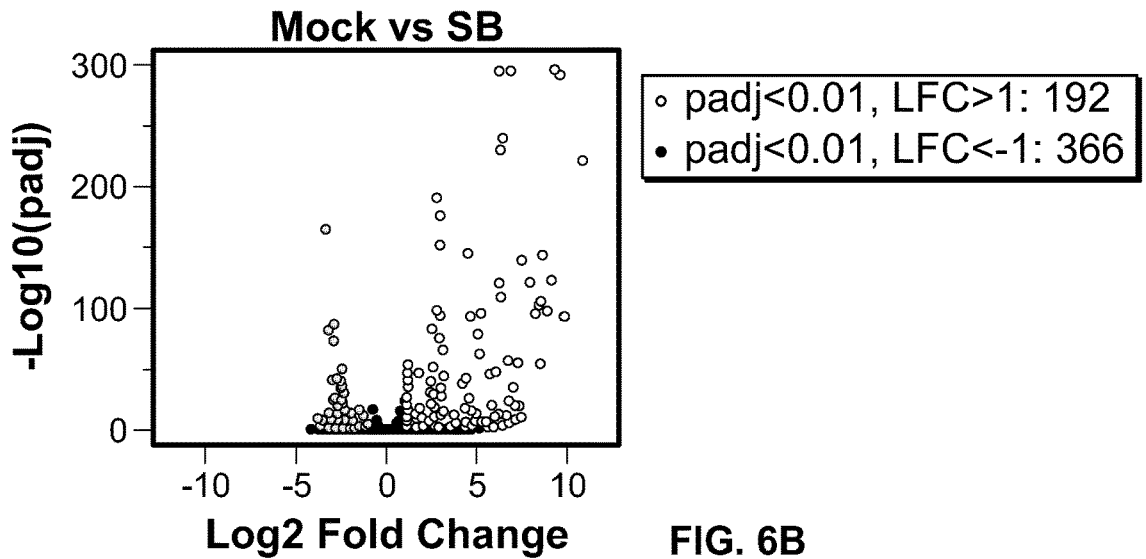
Figure 6C:
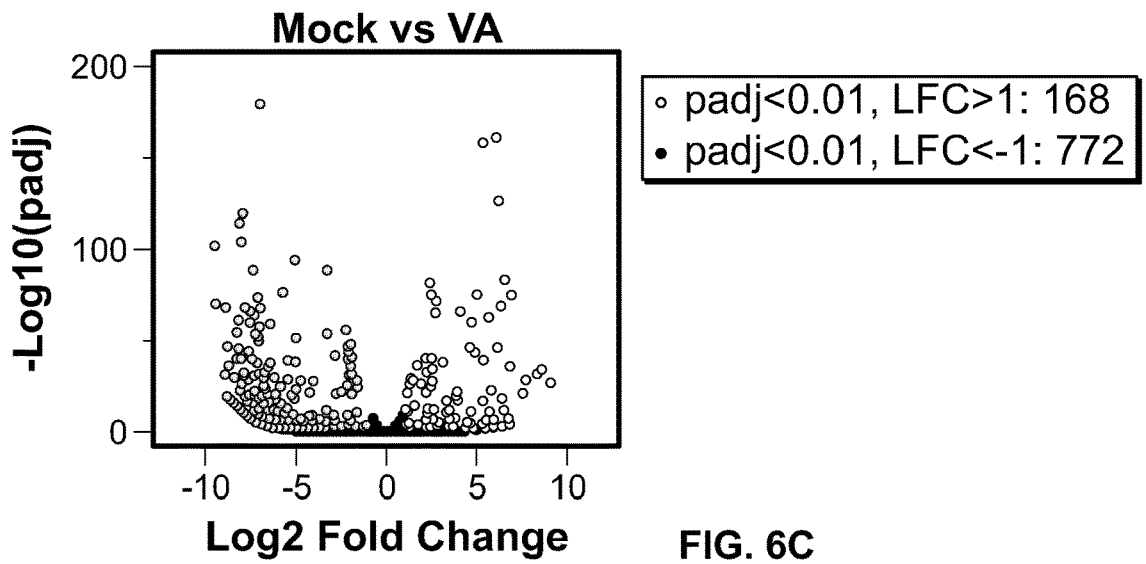
Figure 6D:
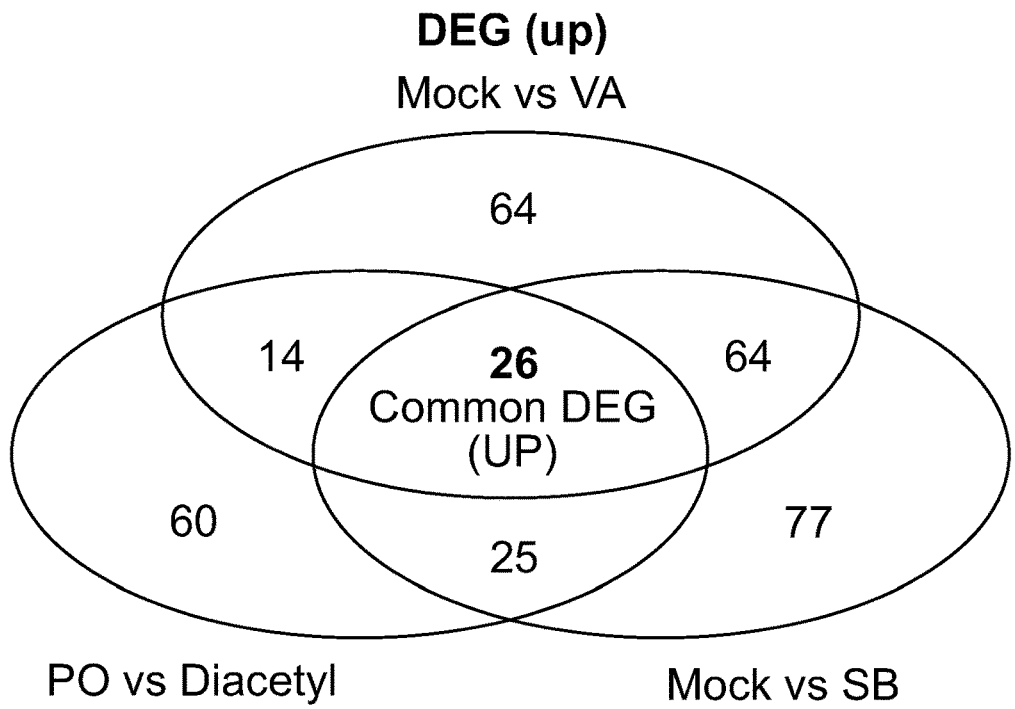
Figure 6E:
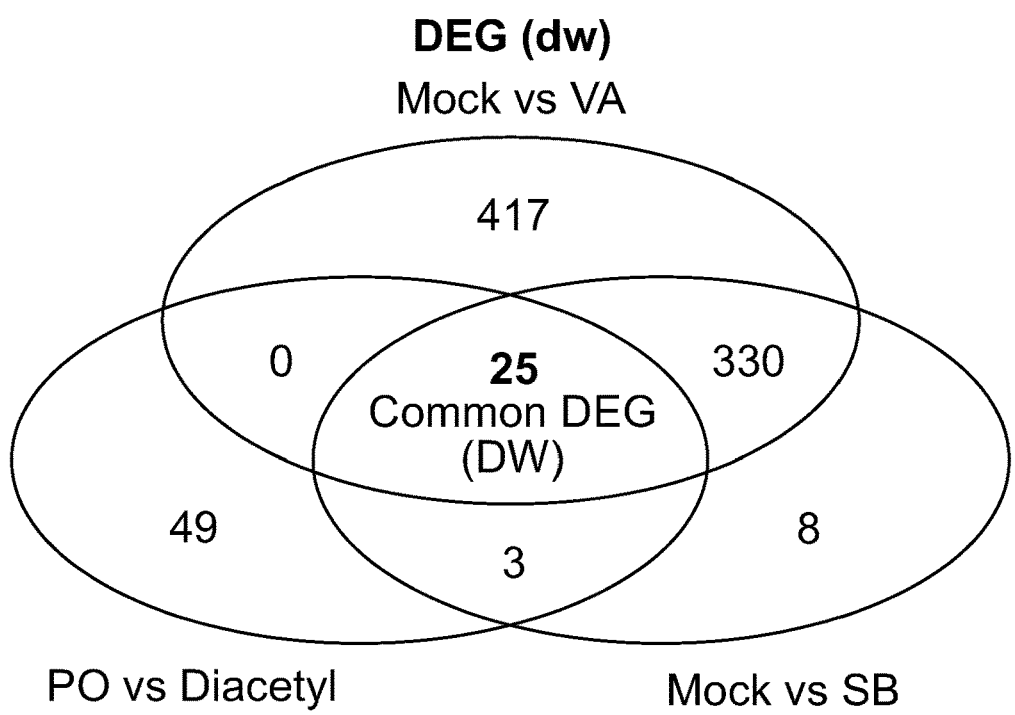
Figure 6F:
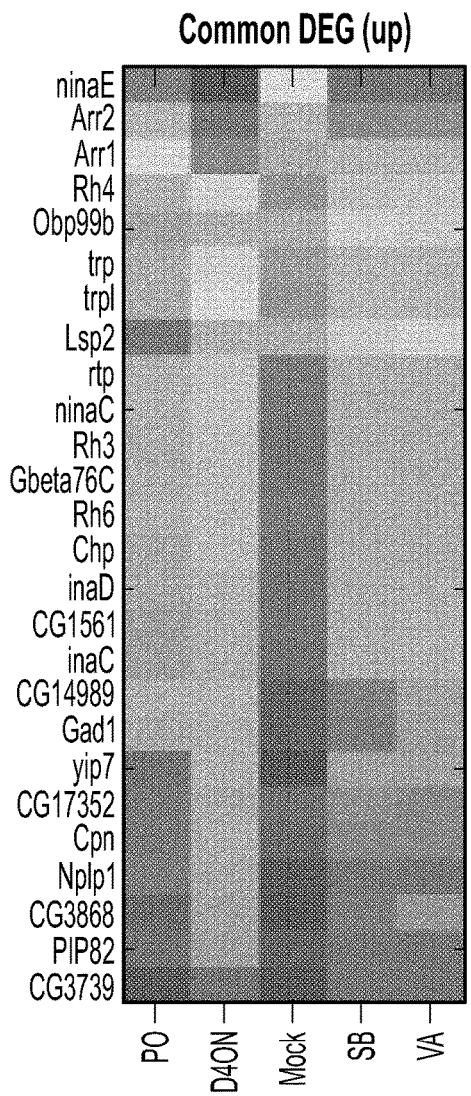
Figure 6G:
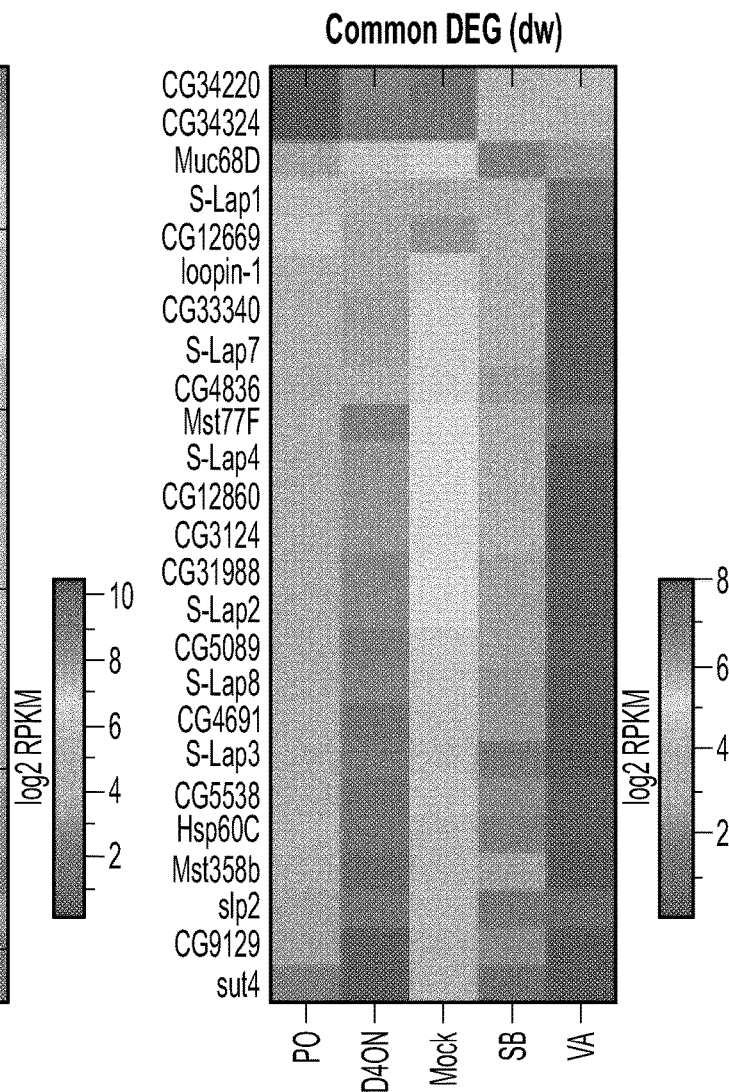
Figure 6H:
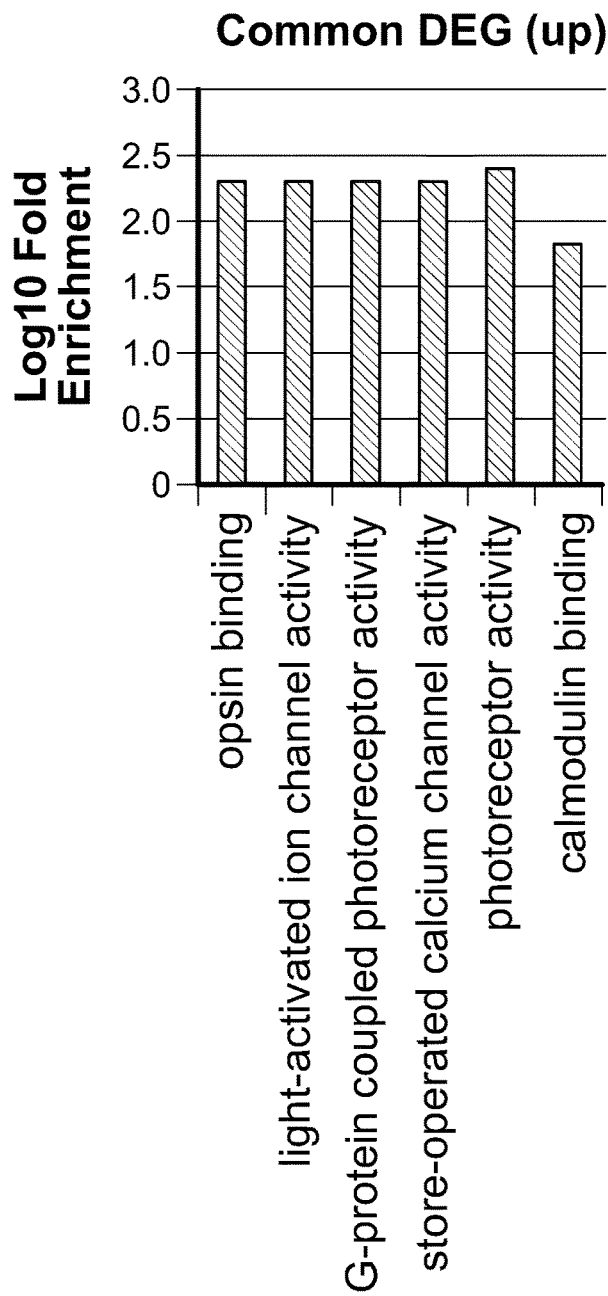
Figure 6I:
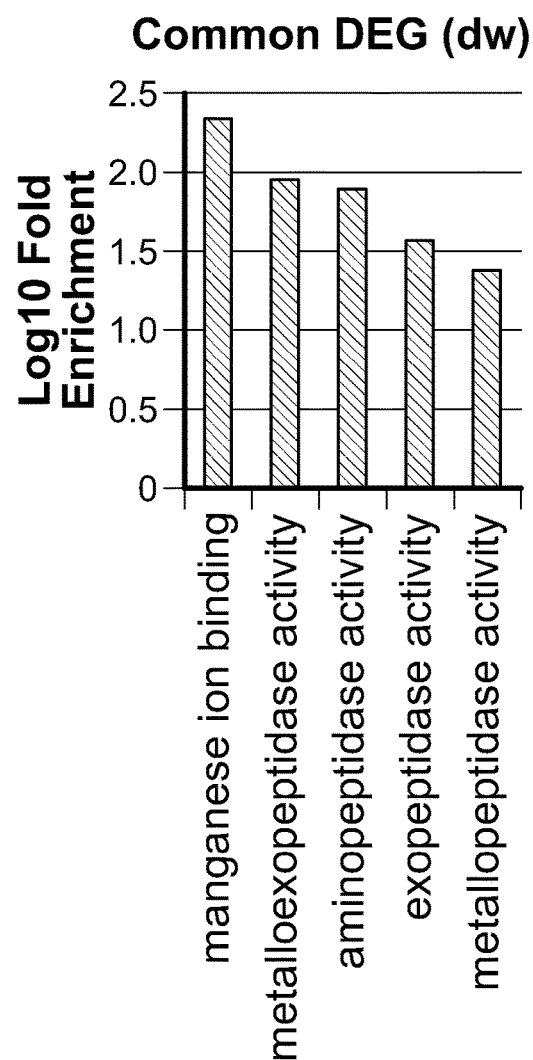

SB feeding induced significant changes in expression levels of 558 genes: 192 genes were >2-fold up-regulated (red dots on the right in FIG. 6B) and 366 genes were >2-fold down-regulated (blue dots on the left in FIG. 6B). The inhibitor VA induced expression changes in 940 genes: 168 genes were >2-fold up-regulated (red dots on the right in FIG. 6C) and 772 genes were >2-fold down-regulated (blue dots on the left in FIG. 6C). >50% of diacetyl up-regulated genes were also up-regulated in either SB or VA treatment conditions. In total, 51 and 40 out of 125 diacetyl-induced genes overlapped with SB- and VA-induced genes, respectively (FIG. 6D). Among those genes, 26 genes were commonly up-regulated upon treatment by all HDAC inhibitors (Common DEG (up), FIGS. 6D-6F). There was reduced overlap among down-regulated genes across these 3 treatments. About 28 out of 77 down-regulated genes in the diacetyl-treated group overlapped with those down-regulated in either the SB- or VA-treated groups, with 25 genes commonly down-regulated across the 3 different treatments (Common DEG (dw), FIGS. 6E-6G). These results are consistent with diacetyl's role as an HDAC inhibitor.

Interestingly, when enrichment of GO terms in Common DEG (up) or (dw) gene lists were examined, several GO terms were found to still be significantly enriched. In the Common DEG (up), "Opsin binding," "light-activated ion channel activity," "G-protein coupled photoreceptor activity," "Store-operated calcium channel activity," "photoreceptor activity," and "calmodulin binding" showed ~100-fold enrichment. Although beyond the scope of this study, surprisingly, several of the gene products represented by these GO terms are likely to participate in visual system function and light detection. Among the Common DEG (dw), "manganese ion binding," "metalloexopeptidase activity," "aminopeptidase activity," "exopeptidase activity," and "metalloexopeptidase activity" showed 5-100-fold enrichment. Taken together, these results indicate that inhibition of HDACs by diacetyl modulates many genes that are regulated by known HDAC inhibitors, as well as several unique genes.

Figure 7A:
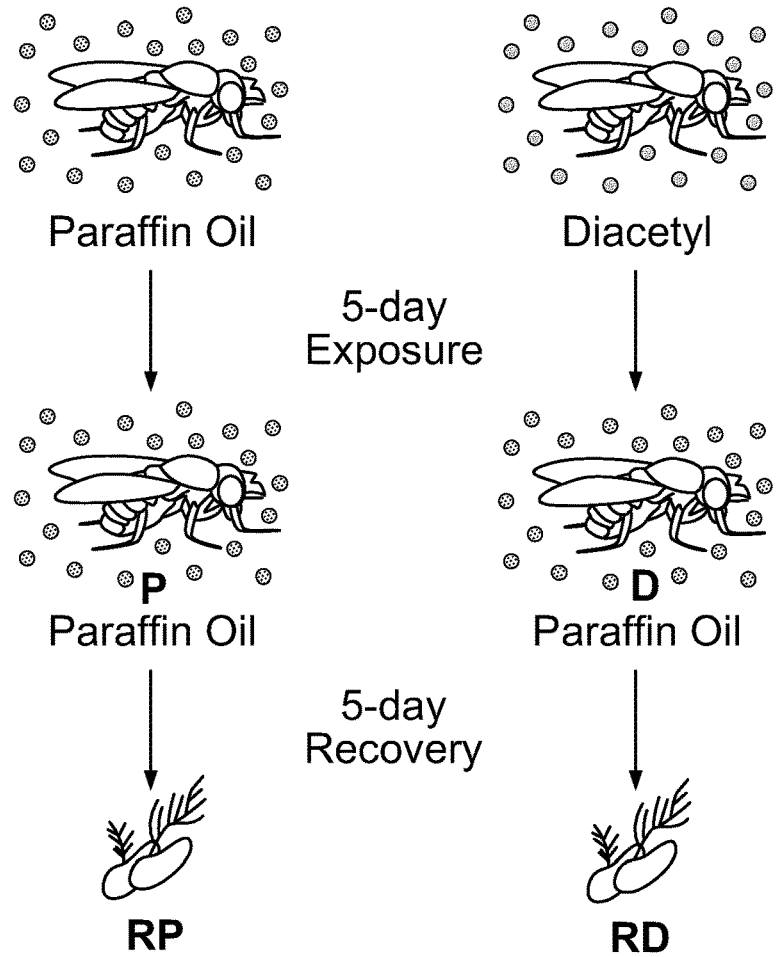
FIGS. 7A-7C demonstrates that HDAC inhibitory effect and gene expression changes can be partially reversed upon odor removal.
Figure 7B:
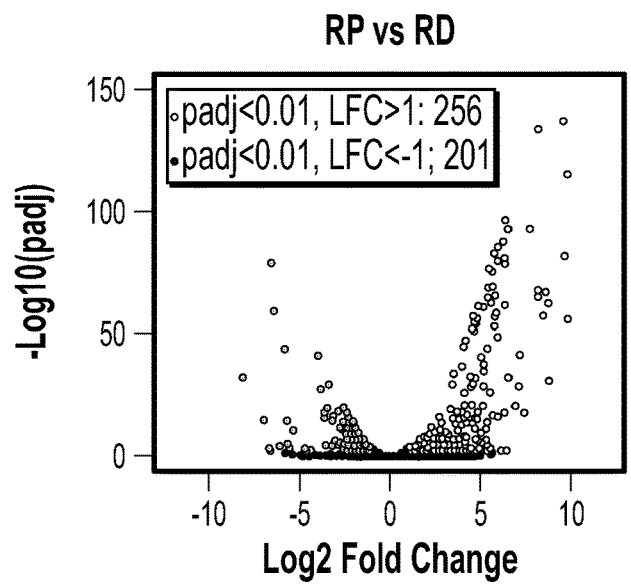
Figure 7C:
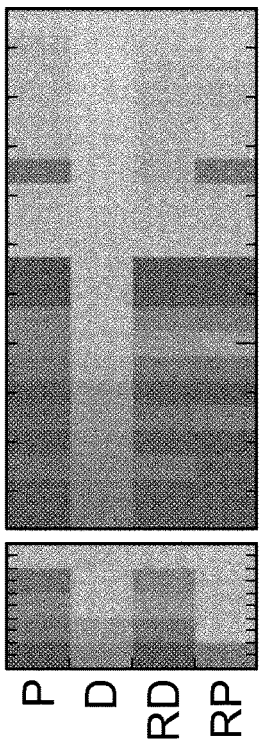
Figure 7C:
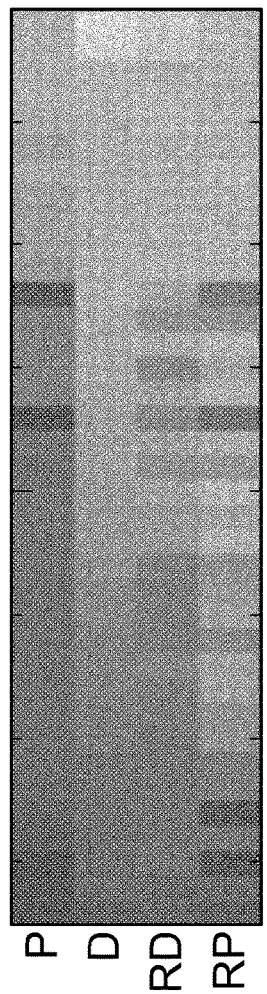
Figure 7C:
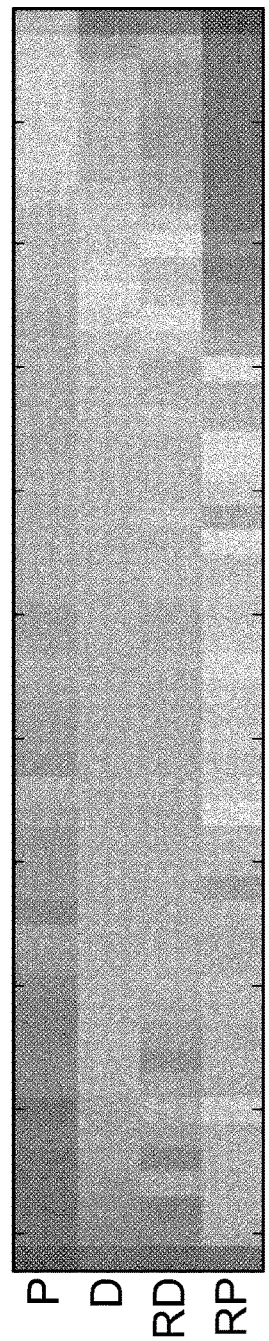
Figure 7C:
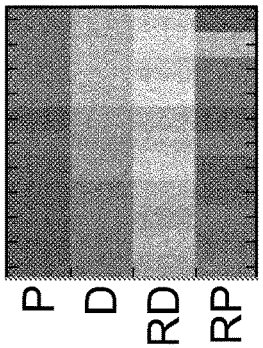
Figure 7C:
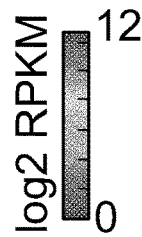
Figure 10A:
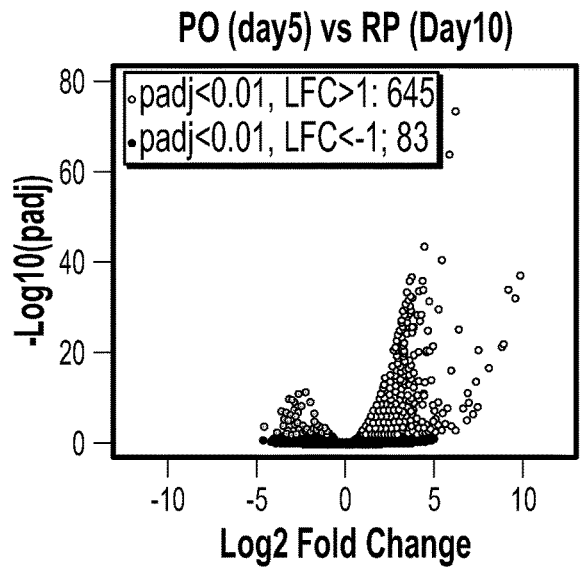
FIGS. 10A-10C show results related to Example 8.
Figure 10B:
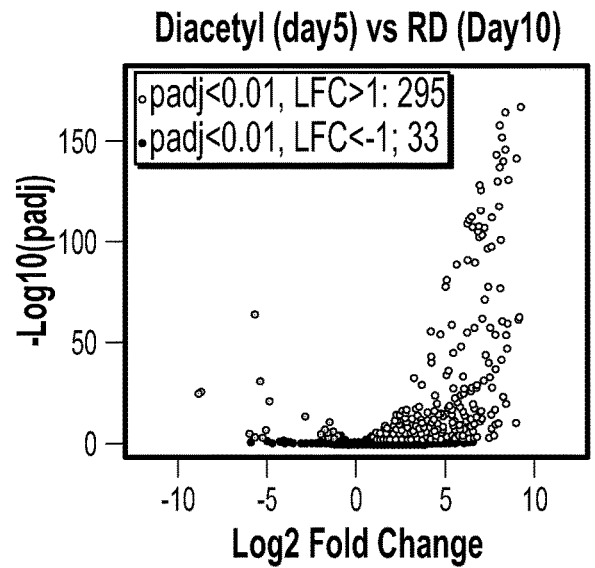
Figure 10C:
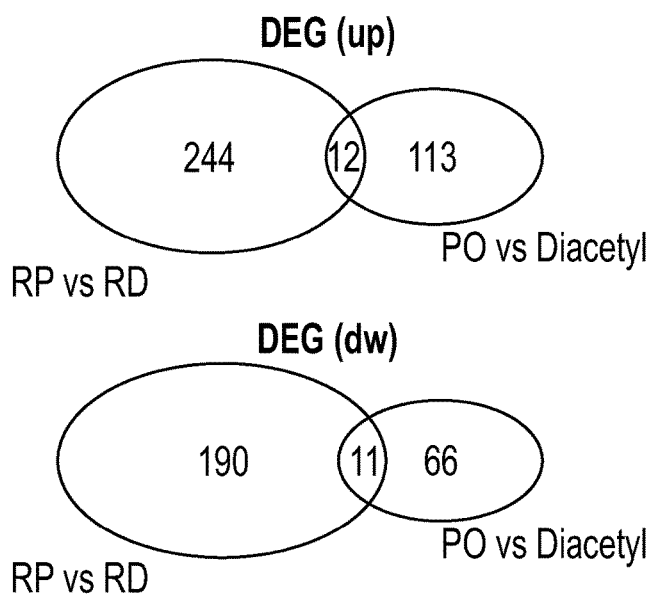

To test whether recovery after diacetyl treatment could also alter gene expression, 5-day diacetyl-exposed flies were maintained on clean media for 5 additional days to reduce the levels of diacetyl in the cells (FIG. 7A). In parallel, age-matched mock experiments were performed with paraffin oil solvent exposure alone. Transcriptome analysis was carried out for the antennae and the differentially-expressed genes were identified (FIG. 7B and FIG. 10). Considering only the 125 genes that were up-regulated after 5-days of diacetyl exposure, the genes fell into 4 categories following recovery (FIG. 7C): 27 transcripts show a reduction with diacetyl recovery; 38 genes show little change; and 11 genes continue to show increased mRNA abundance after odor removal. Additionally, a large number of genes were found that are down-regulated following diacetyl recovery in comparison to the untreated Mock 10 day-old flies (FIG. 7C). These results suggest that the effects of HDAC inhibitory odorant exposure are not permanent but dynamic, and removal of the odorant leads to subsequent changes in gene expression.

The transcriptome analyses of antennae from flies treated with HDAC inhibitors, either diacetyl, sodium butyrate or valproic acid, revealed sets of genes whose expression are potentially normally regulated by HDACs. Interestingly, many of the genes which were commonly up-regulated by these 3 HDAC inhibitors are involved in photoreception. These genes are normally expressed in the photoreceptor cells of the eyes, which are derived from the same imaginal disc as the antennae. A recent study also found expression of visual phototransduction genes in the *Drosophila* auditory organ located in the second segment of the antenna. Spatial and temporal activation of a series of transcription factors are thought to be involved in determining expression of the antenna- or eye-specific genes during development. Our results suggest that the expression of those photoreceptor molecules is normally suppressed by HDAC-mediated histone modifications in the antennae. In the gene fraction, which was commonly down-regulated by these 3 HDAC inhibitors, a specific enzyme family of genes seems to be significantly enriched called the Sperm-Leucyl Amino Peptidases (S-Laps). Seven out of 8 members of the S-Lap gene family (loopin-1 (S-Lap6), S-Lap1-4, 7 and 8) are observed among the genes that are commonly down regulated by HDAC inhibitors. These genes are specifically expressed in the testis and considered to be involved in spermatogenesis. Our results suggest that the expression of these genes may be upregulated as a result of HDAC-mediated histone modifications or other HDAC inhibitor-targeted transcription factors in the antennae under normal conditions.

Example 9

Volatile Diacetyl Protects from Neurodegeneration in Huntington's Model *Drosophila*

In order to test whether the natural HDAC-inhibitory odorant delivered in volatile form has promise for treatment of neurodegenerative disorders, a previously-established *Drosophila* model of human Huntington's disease was used. In this well-established model, the human Huntington protein with expanded poly-Q repeats is expressed in the neurons of the compound eye, causing progressive degeneration of the photoreceptor rhabdomere cells in each ommatidium. Previous studies have shown that orally-administered HDAC inhibitors such as sodium butyrate and SAHA can significantly reduce photoreceptor degeneration in this model.

Figure 8A:
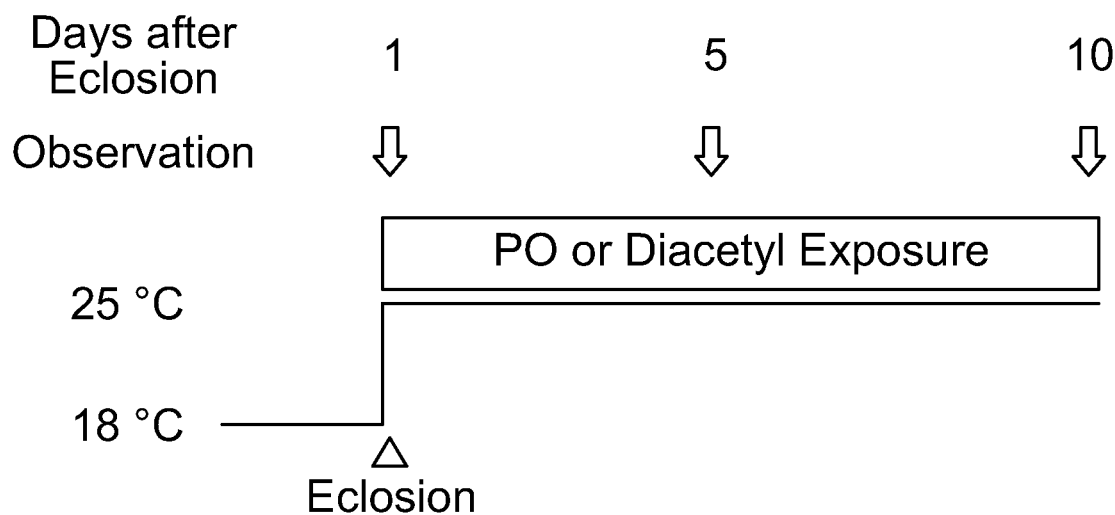
FIGS. 8A-8G demonstrates that diacetyl odorant can prevent neurodegeneration in Huntington's model *Drosophila*.
Figure 8B:
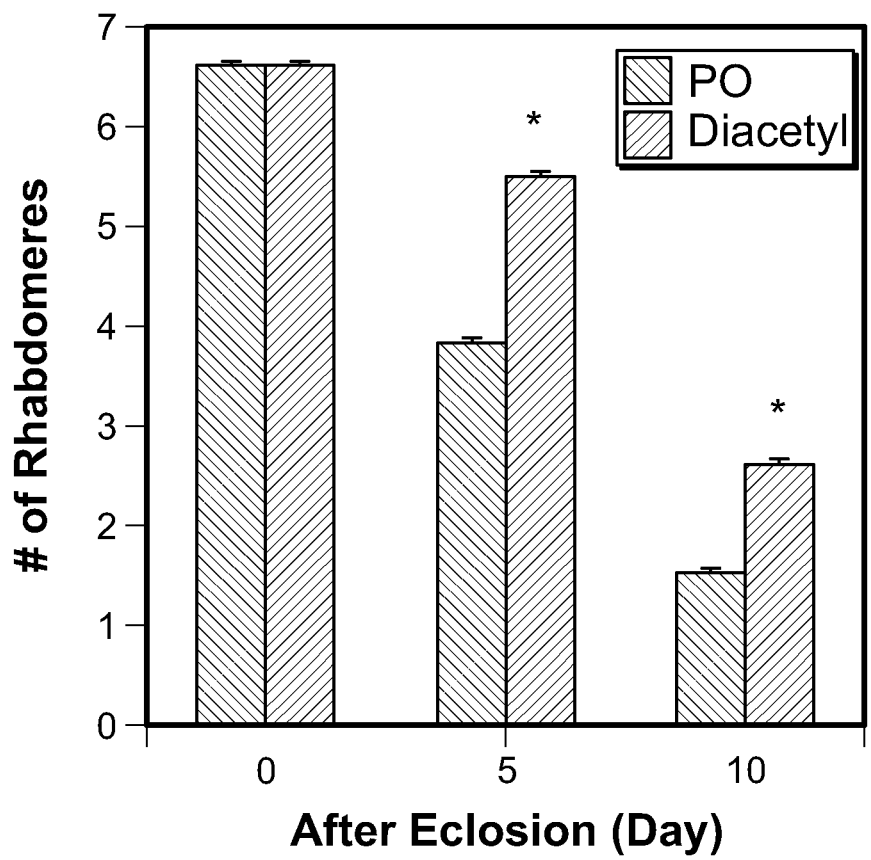
Figure 8C:
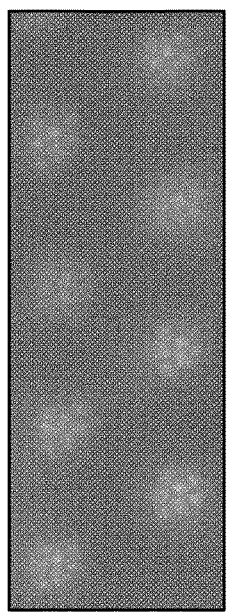

When the transgenic flies expressing two copies of the human Huntington with poly-Q repeats (HTTQ120) under control of the eye-specific GMR promoter were raised at 18° C., the number of rhabdomeres in each ommatidium was similar to that of control flies (7) immediately post-eclosion (day 1, FIGS. 8A-8C). When these flies were moved to 25° C. following eclosion (FIG. 8A), they showed dramatic degeneration of rhabdomeres over a period of 10 days (FIGS. 8B, 8D-8G). The mean number of rhabdomeres was reduced from 7 to ~1 by day 10.

Figure 8D:
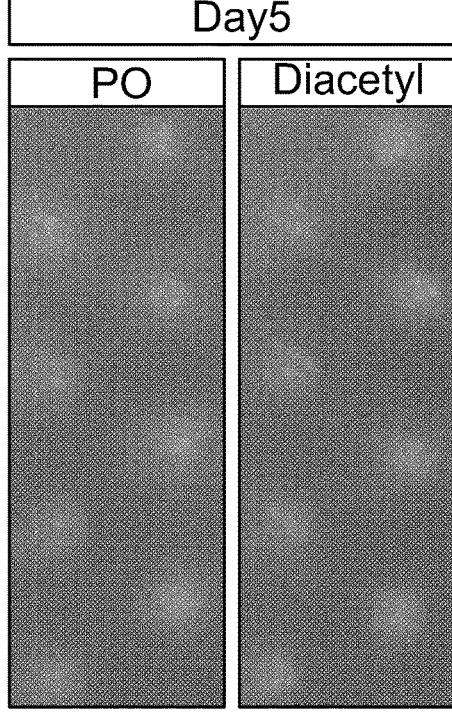
Figure 8E:
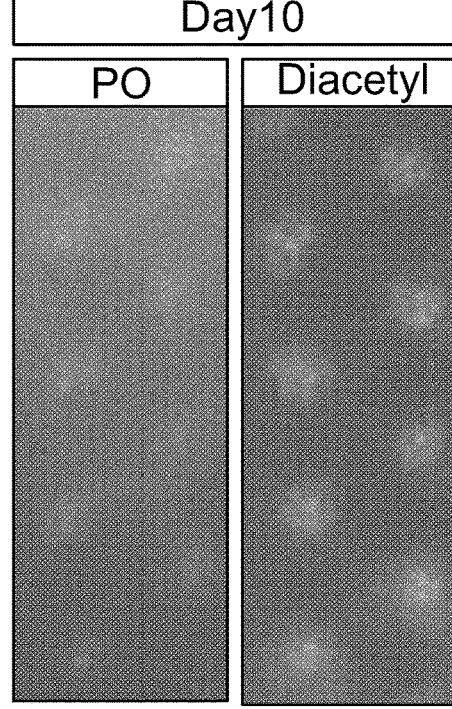
Figure 8F:
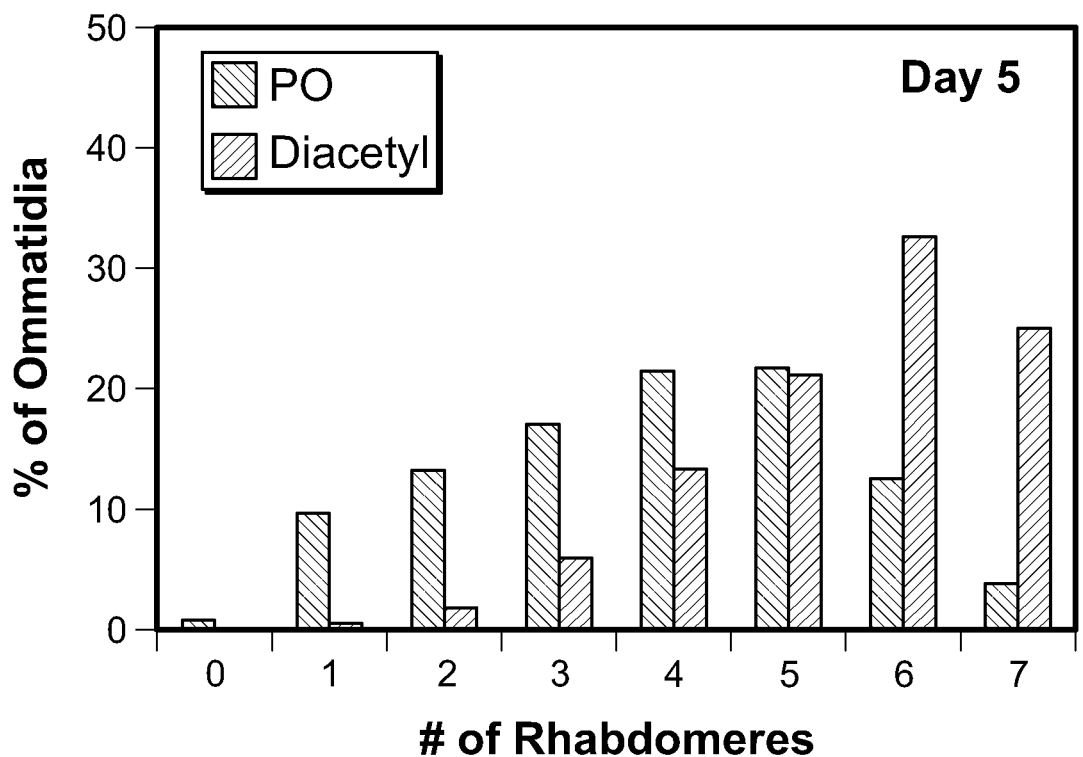
Figure 8G:
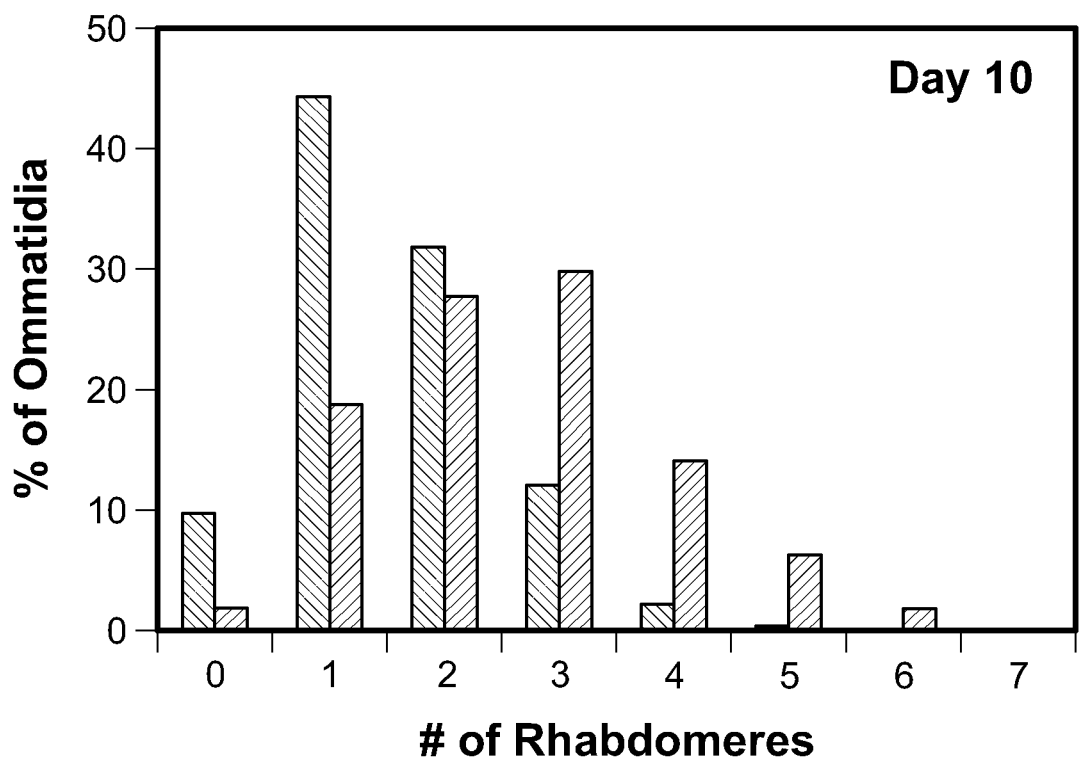
Figure 9:
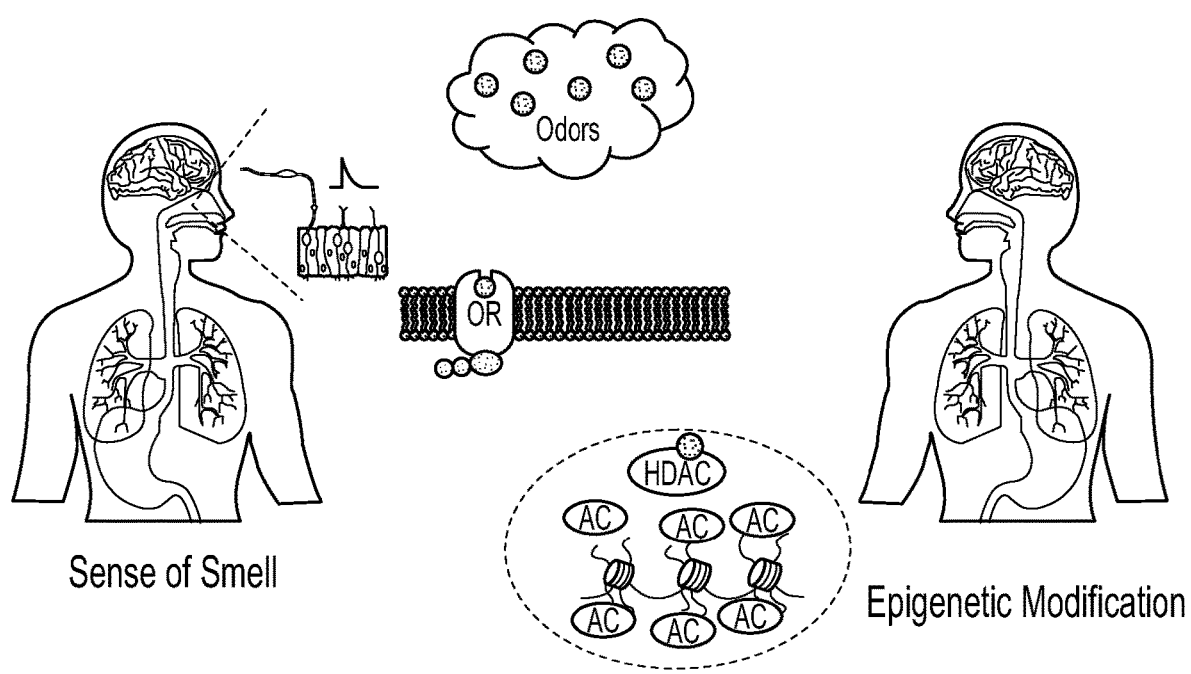
FIG. 9 depicts the model of diacetyl odor effects in an organism. A schematic illustration depicting the 2 pathways through which odorants like diacetyl are likely to act.

Remarkably, when the Huntington (HTTQ120)-expressing flies were exposed immediately after eclosion to volatile headspace of 1% diacetyl (in paraffin oil solvent) (FIG. 8A), they showed a substantial (50%) inhibition of rhabdomere loss (FIGS. 8B, 8D-8G). The majority of ommatidia retained 6-7 rhabdomeres at day 5 (FIGS. 8D and 8F). Even after 10 days, the majority of the ommatidia still had 2-3 rhabdomeres left in the odor-exposed flies, while the solvent controls had only ~1-2 rhabdomeres (FIGS. 8E and 8G). These results demonstrate that diacetyl odorant exposure slows down the photoreceptor degeneration caused in the Huntington's disease model flies. It is thus believed that this odorant may be used as a prophylactic against neurodegenerative disorders.

Furthermore, our finding that diacetyl odor treatment slows down the Huntington's disease symptoms in the fly model indicates that diacetyl treatment can also apply to other types of neurodegenerative diseases such as the polyglutamine (polyQ) diseases. The clinical benefit of HDAC inhibitors for Huntington's diseases has long been suggested by studies using disease model flies and mice, and a few HDAC inhibitors are now under pre-clinical or clinical trials. However, there are still a lot of challenges to overcome, such as transport of HDAC inhibitors through the blood-brain barrier. Due to its volatility and small size, diacetyl odor volatile molecules could be transferred through the intranasal route to the brain, which bypasses the blood-brain barrier. It is further contemplated that odorants may pass through the nasal passage alone, and the beneficial effect of diacetyl against Huntington's disease and other neurodegenerative diseases translate to the mammalian system. Another convenient route for administration of such odor-based therapeutics could be through the lungs. These small molecules would likely have direct access to cells in the lungs and would enter the blood stream rapidly. Any therapeutic potential must be carefully balanced across potential risks, given the deleterious effect of diacetyl "popcorn lung" and its toxicity in cultured cells. Even so, at lower concentrations it is present in several foods we eat, and is still on the GRAS (Generally Regarded as Safe) list for use as flavoring.

Odor Exposure Protocol for Huntington's Disease Model Flies

Figure 11:
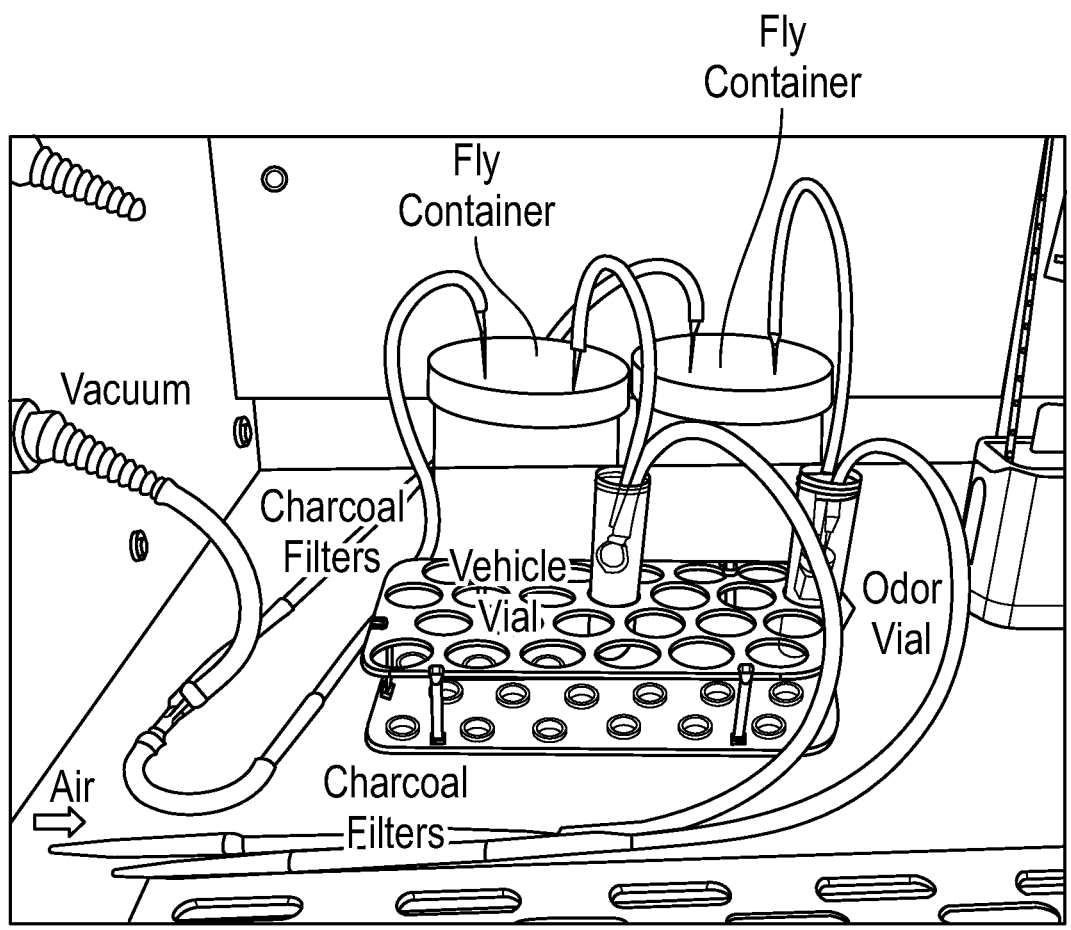
FIG. 11 is an image of odor exposure containers used in Example 9.

Flies were exposed to diacetyl in a cylindrical container (112 mm diameter×151 mm height). Each container was tightly closed but had 2 holes, one of which connected to an air suction port, and the other to a vial containing either of 5 mL paraffin oil or 5 mL 1% diacetyl in paraffin oil. A gentle suction was applied to pull the headspace from the odor or paraffin oil vials into the cylindrical structure (FIG. 11). pGMR-HTTQ120 flies were maintained at 18° C. Adult flies aged 1 d were transferred to fly vials containing fresh medium, and put into the odor-filled container at room temperature. Paraffin oil and 1% diacetyl solution were prepared and replaced every day. At the end of the fifth day of exposure, half of the flies were collected and subjected to pseudopupil analysis. The remaining flies were transferred to fresh medium and exposed to the odors for an additional 5 days. All treatments and experiments were performed at room temperature.

Pseudopupil Analysis

Pseudopupil Analysis was performed according to a protocol described previously (Song et al., 2013). Flies were decapitated and mounted on a microscope slide by dipping in a drop of nail polish. The arrangement of rhabdomeres in the ommatidia of the compound eyes were analyzed with Axio Imager M2 (Carl Zeiss, Oberkochen, Germany) using a 63× objective, and photographed with Axiocam 506 mono (Carl Zeiss). Six hundred ommatidia from 30 eyes of 15 flies were scored for each condition.

What is claimed is:

1. A method for protecting against neurodegeneration in Huntington's disease in a subject in need thereof, comprising administering to the subject via inhalation an effective amount of diacetyl.

2. The method of claim 1, wherein the subject is a mammal.

3. The method of claim 1, wherein the subject is a human.

4. The method of claim 1, wherein the effective amount of diacetyl is nasally administered.

5. The method of claim 1, wherein the effective amount of diacetyl is administered as a gas or vapor.

* * * * *